United States Patent
Simon et al.

(10) Patent No.: US 10,952,390 B2
(45) Date of Patent: *Mar. 23, 2021

(54) CATNIP CULTIVAR 'CR3'

(71) Applicant: Rutgers, The State University of New Jersey, New Brunswick, NJ (US)

(72) Inventors: James E. Simon, Princeton, NJ (US); William Reichert, Branchburg, NJ (US); Qingli Wu, Annadelle, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/719,259

(22) Filed: Dec. 18, 2019

(65) Prior Publication Data

US 2020/0146250 A1    May 14, 2020

Related U.S. Application Data

(63) Continuation of application No. 16/324,088, filed as application No. PCT/US2017/065158 on Dec. 7, 2017, now Pat. No. 10,512,231.

(60) Provisional application No. 62/431,218, filed on Dec. 7, 2016.

(51) Int. Cl.
   *A01H 6/50*   (2018.01)
   *A01H 5/12*   (2018.01)

(52) U.S. Cl.
   CPC .............. *A01H 6/50* (2018.05); *A01H 5/12* (2013.01)

(58) Field of Classification Search
   CPC ........................................................ A01H 6/50
   See application file for complete search history.

(56) References Cited

U.S. PATENT DOCUMENTS

| | | | |
|---|---|---|---|
| 5,682,838 A * | 11/1997 | Reich ................ | A01K 15/025 119/709 |
| 7,381,431 B2 | 6/2008 | Baker et al. | |
| 10,512,231 B2 | 12/2019 | Simon et al. | |
| 2016/0183432 P1 | 6/2016 | Ganzke et al. | |
| 2016/0213730 A1 | 7/2016 | Simon et al. | |
| 2018/0116144 A1 | 5/2018 | Simon | |

OTHER PUBLICATIONS

Schultz et al Environmental Entomology vol. 33, No. 6, pp. 1562-1569 (Year: 2004).*
Amer et al., "Repellency effect of forty-one essential oils against *Aedes, Anopheles*, and *Culex* mosquitoes," *Parasitology Research*, 99:478-490 (2006).
Bernier et al., "Comparison of contact and spatial repellency of catnip oil and N, N-diethyl-3-methylbenzainide (DEET) against mosquitoes," *Journal of Medical Entomology*, 42(3):306-311 (2005).
Birkett et al., "Repellent activity of catmint, Nepeta cataria, and iridoid nepetalactone isomers against Afro-tropical mosquitoes, ixodid ticks and red poultry mites," *Phytochemistry*, 72(1):109-114 (2011).
Cuauhan et al., "A field bioassay to evaluate potential spatial repellents against natural mosquito populations," *Journal of the American Mosquito Control Association*, 28(4):301-306 (2012).
Dong et al., "Determination of Nepetalactones and Dihydronepetalactones in *Nepeta cataria* by LC/MS," 252nd ACS National Meeting & Exposition, Philadelphia, PA, Aug. 21-25, 2016. (1 page).
International Search Report and Written Opinion for PCT/US2017/065158, dated Mar. 6, 2018, by the United States Patent and Trademark Office as ISA (8 pages).
Park et al., "Catnip as a Source of Essential Oils," reprinted from "Issues in new crops and new uses," *ASHS Press*, Alexandria, Virginia, J. Janick and A. Whipkey Editors, pp, 311-315 (2007).
Reichert et al., "Repellency Assesment of *Nepeta cataria* Essential Oils and Isolated Nepetalactones on *Aedes aegypti*," *Scientific Reports*, 9:1524 (9 pages) (2019).
Reichert et al., "'CR9': A New Highly Aromatic Catnip *Nepeta cataria* L. Cultivar Rich in Z, E-Nepetalactone." *HortScience*, 51(5):588-591 (2016).
Reichert et al., "Comparing Headspace Sampling to Distilled Essential Oils for Qualitative Predictions in Catnip Plants," Rutgers Center for Sensory Sciences and Innovation's 3rd Flavors, Fragrances & Perception Symposium. New Brunswick, NJ. Dec. 7, 2015 (1 page).
Schultz et al., "Natural insect repellents: activity against mosquitoes and cockroaches," *Natural Products for Pest Management, ACS Symposium Series* No. 927, pp. 169-181 (2006).

* cited by examiner

*Primary Examiner* — David H Kruse
(74) *Attorney, Agent, or Firm* — Klarquist Sparkman, LLP

(57) ABSTRACT

The disclosure provides seed, tissue cultures, essential oil extracts, and plants of catnip hybrid 'CR3', as well as methods for producing a catnip plants by crossing 'CR3'plants with themselves or with another catnip plant, such as a plant of another genotype, variety, or cultivar. The disclosure further provides seed, tissue cultures, essential oil extracts, and plants produced by such crossing. Methods of using the plants and extracts as insect repellents and in pet toys, are also provided.

15 Claims, 7 Drawing Sheets
(1 of 7 Drawing Sheet(s) Filed in Color)

CATNIP CULTIVAR 'CR3'

CROSS REFERENCE TO RELATED APPLICATIONS

This is a Continuation of U.S. patent application Ser. No. 16/324,088, filed Feb. 7, 2019, and issuing as U.S. Pat. No. 10,512,231 on Dec. 24, 2019, which is a U.S. National Stage of International Application No. PCT/US2017/065158, filed Dec. 7, 2017, which was published in English under PCT Article 21(2), which claims the benefit of U.S. Provisional Application No. 62/431,218 filed Dec. 7, 2016. The entire content of each prior application is incorporated herein by reference in its entirety.

FIELD

The present disclosure provides a new catnip (*Nepeta cataria*) cultivar designated 'CR3', extracts from the variety, and uses of the catnip and its extracts, for example as an insect repellant.

BACKGROUND

Catnip (*Nepeta cataria*, Fam. Lamiaceae), an aromatic herb from southwestern Asia, is best known for causing a euphoric effect on domestic cats and other members of the feline family due to nepetalactones, volatile compounds contained in the essential oil of the plant. The aromatic volatiles of catnip are produced in the glandular trichomes in the leaf epidermis. Because of the morphological nature of the bilabiate bisexual flowers, this plant can self-pollinate as well as outcross. Current production methods utilize seeds and transplants from undomesticated populations, though more recently two cultivars have been developed, each distinctly different from the disclosed 'CR3' cultivar. While well known for modifying felines behavior, the essential oils from *N. cataria* are a potent insect repellent and comparable to the benchmark repellent DEET (Bernier et al., *Med. Entomol.* 42:306-311, 2005). *N. cataria's* essential oil repels mosquitoes that carry the plasmodium for malaria, the yellow fever virus and others.

Catnip's volatile oil effectively repels mosquitoes, including the females that carry the plasmodium causing malaria and those that transmit yellow fever, filariasis, the West Nile virus, and encephalitis, for a total of six different mosquito species repelled (Abdelkrim and Mehlhorn. 2006. *Parasitol. Res.* 99:478-490; Bernier et al., 2005. *Med. Entomol.* 42:306-311; Birkett et al., 2011. *Phytochemistry.* 72:109-114; Chauhan et al., 2012. *J. Amer. Mosquito Control Assn.* 28:301-306). *N. cataria* plants were tested in parallel with 41 other plants and were among the top five most efficient repellents (Abdelkrim and Mehlhorn. 2006. *Parasitol. Res.* 99:478-490).

Nepetalactone, the active ingredient present in catnip plant extracts, occurs as two major isomers: Z, E- and E, Z-nepetalactone. These two diastereomeric isomers are structurally very similar and differ only in the orientation of substituents across one bond.

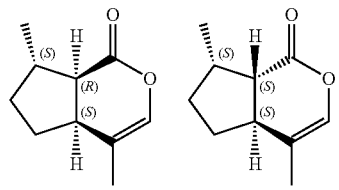

Z,E Nepetalactone    Z,E Nepetalactone

Catnip is largely undomesticated, and little breeding has been undertaken to improve the plant's horticultural traits. Undomesticated populations of *N. cataria* plants do no stand erect and often lie on the soil floor or do not grow sufficiently upright not allowing the use of mechanical harvesters. Catnip is also susceptible to environmental stresses such as cold temperatures and thus in many cases do not survive winter conditions in northern temperate zones or suffers from severe winter injury. There have been two cultivars described as improvements over nondomesticated catnip (Reichert et al., *HortScience.* 51(5):588-591, 2016; US 2016/0183432) that one otherwise finds in seed catalogs or in commercial seed catalogs, and the new variety disclosed herein is distinct from both of those and all others on the commercial marketplace. The two cultivars described as improvements over nondomesticated catnip were identified as rich in Z, E-nepetalactone while the disclosed 'CR3' variety was purposefully bred to be rich in E, Z-nepetalactone, while still accumulating Z, E-nepetalactone. While originally selecting *N. cataria* populations for physical structure and ease of mechanical harvesting, focus shifted toward creating a catnip cultivar with high economical impact and a specific unique chemical profile. The 'CR3' variety also produces uniform seeded progeny allow farmers to decrease their costs by not using higher cost transplants. The use of transplants is more costly due to the production and labor costs associated with them. Commercialization of *N. cataria* plants for biomass, essential oil, and E, Z-nepetalactone for pet and new insect repellent products remains challenging.

SUMMARY

The inventors collected *N. cataria* populations for over a decade and beginning in 2004, began selection and breeding studies relative to improving the growth and production, biomass and essential oils in order to create new catnips that could significantly improve the commercialization of catnip for its production of essential oil, to improve and modify the chemical composition of the essential oil and of the nepetalactones to make it more effective and with improved desirable phenotypic characteristics to create a more economical catnip cultivar that produces high yields in E, Z-nepetalactone. Two prior cultivars described as improvements over nondomesticated catnip were identified as rich in Z, E-nepetalactone while the disclosed 'CR3' cultivar was bred to be rich in E, Z-nepetalactone while still accumulating significant Z, E-nepetalactone (Reichert et al., *HortScience.* 51(5):588-591, 2016; US 2016/0183432). While originally selecting *N. cataria* populations for physical structure and ease of mechanical harvesting, focus shifted toward creating a catnip cultivar with high economical impact and a specific unique chemical profile. The disclosed 'CR3' cultivar also produces uniform seeded progeny allow farmers to decrease their costs by not using higher cost transplants. The use of transplants is more costly due to the production and labor costs associated with them.

The present disclosure provides a new catnip cultivar 'CR3' with increased amounts of total essential oil and E, Z-nepetalactone yields than other varieties. Currently, there are no *N. cataria* cultivars that produce large amounts of the E, Z-nepetalactone isomer. Also provided herein are methods of producing 'CR3', for example using somaclonal variations in plant tissue culture and protoplast culture conditions as well as induced mutagenesis technologies. The disclosure also provides extracts from 'CR3', methods of making such extracts, and methods of using 'CR3' and its extracts, for example in pet toys and as an insect repellant.

'CR3' catnip seed was deposited with the American Type Culture Collection (ATCC), 10801 University Blvd., Manassas, Va., 20110 on Dec. 7, 2016 under ATCC Accession No. PTA-123728. The deposit is intended to meet all of the requirements of 37 C.F.R. §§ 1.801-1.809. Access to the deposit will be available during the pendency of the application to the Commissioner of Patents and Trademarks and persons determined by the Commissioner to be entitled thereto upon request. The deposit will be maintained in the depository for a period of 30 years, or 5 years after the last request, or for the effective life of the patent, whichever is longer, and will be replaced if necessary during that period. Applicants do not waive any infringement of rights granted under this patent or under the Plant Variety Protection Act (7 U.S.C. 2321 et seq.).

Provided herein is a catnip plant 'CR3' having significantly increased levels of E, Z-nepetalactone, as well as progeny of such plants, plant parts, including leaves, cells, plant protoplasts, plant cells of a tissue culture from which catnip plants can be regenerated, plant calli, plant clumps, and plant cells that are intact in plants or parts of plants, such as pollen, ovules flowers, seeds, leaves, stems, roots and the like. Also provided is plurality of 'CR3' catnip plants grown in a field. In addition to the 'CR3' plant, derivatives of such plants retaining elevated levels of E, Z-nepetalactone are provided. In one example, the disclosure provides catnip plants having the genotype of one of the new variety disclosed herein. For example, the disclosure provides plants produced by growing the seed of the new catnip variety disclosed herein.

The disclosure provides a tissue culture of regenerable cells of the new 'CR3' varitey, as well as plants regenerated therefrom. Such regenerated catnip plants can include, consist essentially of, or consist of the physiological and morphological characteristics of a plant grown from the seed of the new 'CR3' varitey disclosed herein. Exemplary regenerable cells include but are not limited to those from protoplasts or cells, such as those from leaf, stem, protoplast, pollen, ovule, embryo, cotyledon, hypocotyl, meristematic cell, root, root tip, pistil, anther, flower, petal, seed, shoot, stein, or petiole of the new 'CR3' varitey provided herein.

The disclosure provides catnip plants having, consisting essentially of, or consisting of, the morphological and physiological characteristics of the new 'CR3' variety provided herein, such as the characteristics noted in Tables 2-5, for example elevated levels of E, Z-nepetalactone as compared to other catnip varieties. In some examples, elevated E, Z-nepetalactone level includes, by percent total essential oils, at least about 59% E, Z-nepetalactone. In some examples, a catnip plant provided herein has an elevated E, Z-nepetalactone level, such as at least 45%, at least 50%, at least 55%, at least 59%, at least 60%, at least 61%, at least 62%, at least 63%, at least 64%, at least 65%, at least 66%, at least 67%, at least 68%, at least 69%, at least 70%, or at least 75% E, Z-nepetalactone as a percent of the relative total essential oils, such as 45% to 70% E, Z-nepetalactone as a percent of the relative total essential oils, 45% to 65% E, Z-nepetalactone as a percent of the relative total essential oils, or 45% to 60% E, Z-nepetalactone as a percent of the relative total essential oil, in its chemical profile (such as 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74% or 75% E, Z-nepetalactone as a % of the relative total essential oils). In other embodiments, a plant or part thereof (such as an essential oil extract) provided herein includes a chemical profile as set forth herein, for example as provided in Table 4. For example, the essential oil composition of such a plant may include a chemical profile comprising about 3% α-pinene, about 29% Z, E-nepetalactone, about 59% E, Z-nepetalactone and about 3.5% β-carophyllene, each as a % of the total essential oil.

Compositions that include a seed that produces a plant of the disclosure in plant seed growth media are provided. Examples of plant seed growth media include soil and synthetic cultivation medium (e.g., those that include polymers and/or hydrogels), and others known in the art (e.g., see U.S. Pat. No. 4,241,537). The growth media can be in a container or can, for example, be soil in a field. Plant seed growth media can provide adequate physical support for seeds and can retain moisture and/or nutritional components. Examples of characteristics for soils that may be desirable can be found, for instance, in U.S. Pat. Nos. 3,932,166 and 4,707,176.

Also provided is a tissue culture of regenerable cells of a disclosed catnip plant, such as one with at least about 45% E, Z-nepetalactone as a % of the relative total essential oils (such as at least 50%, at least 55%, at least 59%, at least 60%, at least 61%, at least 62%, at least 63%, at least 64%, at least 65%, at least 66%, at least 67%, at least 68%, at least 69%, at least 70%, or at least 75% E, Z-nepetalactone as a % of the relative total essential oils), as well as plants regenerated therefrom which may express all the physiological and morphological characteristics of the disclosed plant.

Disclosed is a catnip plant, such as one with at least about 59% E, Z-nepetalactone content, which includes a single locus conversion. The single locus conversion can include a transgenic gene which has been introduced by genetic transformation. In some embodiments, the single locus conversion can include a dominant or recessive allele. The locus conversion can confer potentially any trait upon the single locus converted plant, including nutritional value, aromatic value, herbicide resistance, insect resistance, resistance to bacterial, fungal, or viral disease, male fertility or sterility, and improved nutritional quality.

A first generation (F1) hybrid catnip seed produced by crossing a plant of the disclosure to a second catnip plant is provided. Also provided are the F1 hybrid catnip plants grown from the hybrid seed produced by such crossing, and the seeds of an F1 hybrid plant. In some embodiments, the $F_1$ hybrid catnip plant is grown from the hybrid seed produced by crossing the new catnip variety provided herein to a second catnip plant. In specific examples, provided is a seed of an $F_1$ hybrid plant produced with the new catnip variety provided herein as one parent, the second generation ($F_2$) hybrid catnip plant grown from the seed of the $F_1$ hybrid plant, and the seeds of the $F_2$ hybrid plant.

Methods of producing catnip seeds are provided. Such a method can include crossing the new catnip variety to any second catnip plant, including itself or another plant of the disclosure. In particular embodiments, the method of crossing includes (a) planting seeds of a plant provided herein; (b) cultivating catnip plants resulting from the seeds until said plants bear flowers; (c) allowing fertilization of the flowers of said plants; and d) harvesting seeds produced from said plants.

Methods of producing hybrid catnip seeds are provided. Such methods can include crossing the new catnip variety to a second, distinct catnip plant which is nonisogenic to the new catnip variety. In particular examples, crossing includes cultivating catnip plants grown from seeds of the new variety provided herein and cultivating catnip plants grown from seeds of a second, distinct catnip plant until the plants bear flowers; cross-pollinating a flower on one of the two plants with the pollen of the other plant; and harvesting the seeds resulting from the cross pollinating.

Method for developing a catnip plant in a catnip breeding program are provided. Such methods can include using the disclosed new catnip plant or parts as a source of breeding material using plant breeding techniques, such as recurrent selection, mass selection, bulk selection, backcrossing, pedigree breeding, genetic marker-assisted selection, and genetic transformation. In certain examples, the catnip plant of the new catnip variety is used as a male or female parent.

Method of producing a catnip plant derived from a plant provided herein, such as an inbred catnip plant, are provided. Such methods can include (a) preparing a progeny plant derived from a plant of the new catnip variety by crossing the plant with a second catnip plant; and (b) crossing the progeny plant with itself or a second plant to produce a progeny plant of a subsequent generation which is derived from a plant of the new catnip variety. The method can further include (c) crossing the progeny plant of a subsequent generation with itself or a second plant; and (d) repeating steps (b) and (c) for, least 2 additional generations (such as at least 3, at least 5, or at least 10 additional generations) to produce an inbred catnip plant derived from a plant of the new catnip variety.

Methods of producing a catnip plant derived from a plant of the new catnip variety can include (a) crossing a derived catnip plant with itself or another catnip plant to yield additional derived progeny catnip seed; (b) growing the progeny catnip seed of step (a) under plant growth conditions to yield additional derived catnip plants; and (c) repeating the crossing and growing steps of (a) and (b) to generate further catnip plants. In specific embodiments, steps (a) and (b) may be repeated from 0 to 7 times (such as 0 to 4 or 1 to 5 times, such as 1, 2, 3, 4, or 5 or more times) as desired to generate further catnip plants derived from a new catnip variety provided herein.

Methods of producing catnip seed from the new catnip plant provided herein are provided. In some examples such methods include crossing the catnip variety provided herein with itself or a second catnip plant and harvesting a resulting catnip seed. In some examples, the catnip plant has a desirable trait, which is introduced into plants and seeds resulting from such a cross. For example, the second plant can be transgenic, wherein the transgene confers the desirable trait. Seeds produced by such methods, including $F_1$ hybrid seeds, as well as catnip plants or parts thereof produced by growing such a seed, are provided. In some examples, the method of crossing includes planting seeds of the catnip variety provided herein, cultivating catnip plants resulting from the seeds until the plants bear flowers, allowing fertilization of the flowers of the plants; and harvesting seeds produced from the plants.

Methods are provided for producing a plant of the catnip variety provided herein that has one or more added desired agronomic traits, as well as plants and seeds generated from such methods. In one example, such a method provides a catnip plant having a single locus conversion of the catnip variety provided herein, wherein the catnip plant includes or expresses the physiological and morphological characteristics of the new catnip variety provided herein (such as those shown in any of Tables 2-4). Such methods can include introducing one or more transgenes that confer one or more desired traits into a plant of the new catnip variety provided herein. A transgenic or non-transgenic single locus conversion can also be introduced by backcrossing. Exemplary desired traits include herbicide tolerance or resistance, resistance or tolerance to an insect, resistance or tolerance to a bacterial disease, resistance or tolerance to a viral disease, resistance or tolerance to a fungal disease, resistance or tolerance to a nematode, resistance or tolerance to a pest, male sterility, site-specific recombination; abiotic stress tolerance (such as tolerance to drought, heat, cold, low or high soil pH level, and/or salt), modified nepetalactone content, such as increased E, Z-nepetalactone content, or other desired qualities.

Methods of introducing a single locus conversion (such as a desired trait) into the new catnip variety disclosed herein are provided. In some examples the methods include (a) crossing a plant of the new catnip variety disclosed herein with a second plant having one or more desired traits to produce $F_1$ progeny plants; (b) selecting $F_1$ progeny plants that have the desired trait to produce selected $F_1$ progeny plants; (c) crossing the selected progeny plants with at least a first plant of variety of one of the new catnip variety disclosed herein to produce backcross progeny plants; (d) selecting backcross progeny plants that have the desired trait and physiological and morphological characteristics of one of the new catnip variety disclosed herein to produce selected backcross progeny plants; and (e) repeating steps (c) and (d) one or more times in succession to produce selected second or higher backcross progeny plants that include the desired trait and the physiological and morphological characteristics of one of the new catnip variety disclosed herein when grown in the same environmental conditions. In some embodiments, the single locus confers a desirable trait, such herbicide tolerance or resistance, drought tolerance, heat tolerance, low or high soil pH level tolerance, salt tolerance, resistance or tolerance to an insect, resistance or tolerance to a bacterial disease, resistance or tolerance to a viral disease, resistance or tolerance to a fungal disease, resistance or tolerance to a nematode, resistance or tolerance to a pest, male sterility, site-specific recombination, abiotic stress tolerance (such as tolerance to drought, heat, low or high soil pH level, and/or salt), modified nepetalactone content, such as increased E, Z-nepetalactone content. In some examples, the single locus confers the ability to synthesize a protein encoded by a gene located within the single locus.

The disclosure also provides catnip plants and parts thereof produced by any of the methods disclosed herein. In some embodiments, the catnip plants produced by the disclosed methods includes at least two, at least three, at least four, at least five, or at least 10 of the traits of a new catnip variety as described herein. In some embodiments, the catnip plants produced by the disclosed methods includes at least two, at least three, at least four, at least five, or at least 10 of the traits of the new catnip variety provided herein (see Tables 2-4), such as an E, Z-nepetalactone content of at least about 45% (such as at least 50%, at least 55%, or at least 59%) by percent total essential oils, as described herein.

The disclosure provides catnip seed deposited as ATCC Accession No. PTA-123728, as well as catnip seed mixtures containing such seeds.

Methods are provided for producing and using an extract from the new catnip variety provided herein. For example, a 'CR3' essential oil extract can be used to induce euphoria in domestic felines. In some examples, such an extract can be used to repel insects, such as those that serve as vectors for pathogens, such as mosquitoes and ticks.

Also provided herein is packaging material containing the 'CR3' plant or parts thereof (such as biomass, leaves, or oils). Such packaging material includes but is not limited to boxes, plastic bags, bottles, or other containers routinely used for catnip or oil. For example, the disclosure provides packages of the 'CR3' plant or parts thereof (such as bags containing 'CR3' leaves and/or biomass). The leaves and/or biomass of 'CR3' may be combined with leaves and/or biomass of other catnip varieties. In one example, the 'CR3' plant or parts thereof (such as biomass or leaves) are part of a pet toy, such as one made of fabric and/or plastic.

An essential oil extract of 'CR3' is also provided, such as one that includes E, Z-nepetalactone. In some examples, such an extract includes DNA and/or protein from 'CR3' plants. In some examples, such an extract includes more E, Z-nepetalactone than Z, E-nepetalactone. Such an extract can be used as an insect repellent, such as a mosquito repellant, such as for *Aedes aegypti* and/or *Anopheles gambiae* mosquitos and/or against other insect pests and mites on humans. In some examples, the repellent is used to repel ticks, such as *Dermacentor variabilis, Rhipicephalus appendiculatus*, and/or *Ixodes scapulari*. In some examples, the essential oil extract of 'CR3' is part of a spray, lotion, stick, cream, disposable wipe, or collar which can be applied to a body (such as a mammal, such as a human, cat or dog) to repel insects. For example, the CR3 oil can be the bioactive ingredient in a composition (which can include other natural or synthetic ingredients), which can be applied to a body (such as a mammal, such as a human, cat or dog) or wore on/around the body of a human or animal to repel insects (such as collars, bags, pouches, clip ons, and the like).

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
FIG. 1 is a digital image showing the disclosed catnip cultivar 'CR3'.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a plant" includes one or a plurality of such plants. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties sought to be obtained by a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

Backcross: The mating of a hybrid to one of its parents. For example hybrid progeny, for example a first generation hybrid ($F_1$), can be crossed back one or more times to one of its parents. Backcrossing can be used to introduce one or more single locus conversions (such as one or more desirable traits) from one genetic background into another.

Biomass: Organic matter derived from an organism, such as a catnip plant or part thereof. In some examples, biomass refers to all the above ground plant material at a particular point of time, thus including the leaves, stems and may include flowers (at varying stages of development given the flowering period ranges over a period of time). Biomass can include all vegetative and reproductive material produced by the plant at time of harvest.

Catnip plant: As used herein, catnip (or sometimes referred to as catmint) refers to any plant from the genus *Nepeta*, which may include but is not limited to *Nepeta cataria*. As used herein, catnip may also refer to a variant, progeny, or offspring of such a plant, including a plant or part thereof. The terms variety, cultivar, or the like may be used interchangeably to refer to a plant of the present disclosure.

Cell. Cell as used herein includes a plant cell, whether isolated, in tissue culture or incorporated in a plant or plant part.

Cross. Synonymous with hybridize or crossbreed. Includes the mating of genetically different individual plants, such as the mating of two parent plants.

Cross-pollination: Fertilization by the union of two gametes from different plants.

Essential oil (EO): A concentrated hydrophobic liquid containing volatile aroma compounds from aromatic plants, such as a catnip plant. An oil is "essential" in the sense that it historically was considered by some to be the "essence of" the plant's fragrance; it does not mean indispensable. The essential oil of catnip is naturally occurring and accumulates in glandular trichomes in leaves and flowers of the catnip/catmint plant. Methods of generating or obtaining an EO from a plant include extraction by distillation (e.g., by using steam or water), expression, solvent extraction, absolute oil extraction, super critical fluid extraction, cold pressing, or combinations thereof.

$F_1$ hybrid: The first generation progeny of the cross of two stable parents that are nonisogenic or isogenic plants.

Gene Silencing. A general term describing epigenetic processes of gene regulation, including any technique or mechanism in which the expression of a gene is prevented.

Genotype. The genetic constitution of a cell, an organism, or an individual (i.e., the specific allele makeup of the individual) usually with reference to a specific character under consideration.

Plant: Includes reference to an immature or mature whole plant, including a plant from which seed, roots or leaves have been removed. Seed or embryo that will produce the plant is also considered to be the plant.

Plant parts. Includes protoplasts, leaves, stems, roots, root tips, anthers, pistils, seed, embryo, pollen, ovules, cotyledon, hypocotyl, flower, shoot, tissue, petiole, cells, meristematic cells and the like. Includes plant cells of a tissue culture from which catnip plants can be regenerated.

Progeny. Offspring; descendants.

Regeneration. The development of a plant from tissue culture. The cells may, or may not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Self-pollination: The transfer of pollen from the anther to the stigma of the same plant.

Single locus converted (conversion) plant: Plants developed by backcrossing and/or by genetic transformation, wherein essentially all of the desired morphological and physiological characteristics of a catnip variety are recovered in addition to the characteristics of the single locus transferred into the variety via the backcrossing technique and/or by genetic transformation.

Tissue culture: A composition that includes isolated cells of the same or a different type or a collection of such cells organized into parts of a plant.

Transformation. The introduction of new genetic material (e.g., exogenous transgenes) into plant cells. Exemplary mechanisms that are to transfer DNA into plant cells include (but not limited to) electroporation, microprojectile bombardment, *Agrobacterium*-mediated transformation and direct DNA uptake by protoplasts.

Transgene. A gene or genetic material that has been transferred into the genome of a plant, for example by genetic engineering methods. Exemplary transgenes include cDNA (complementary DNA) segment, which is a copy of mRNA (messenger RNA), and the gene itself residing in its original region of genomic DNA. In one example, describes a segment of DNA containing a gene sequence that is introduced into the genome of a catnip plant or plant cell. This non-native segment of DNA may retain the ability to produce RNA or protein in the transgenic plant, or it may alter the normal function of the transgenic plant's genetic code. In general, the transferred nucleic acid is incorporated into the plant's germ line. Transgene can also describe any DNA sequence, regardless of whether it contains a gene coding sequence or it has been artificially constructed, which has been introduced into a plant or vector construct in which it was previously not found.

New Catnip Plant with Increased Essential Oils

The disclosure provides methods and compositions relating to plants, seeds, and derivatives of catnip (*Nepeta cataria*) 'CR3'. Catnip cultivar 'CR3' was developed specifically for commercial agricultural production with a more upright growth habit and higher biomass, essential oil, and with a purposefully bred elevated level of E, Z-nepetalactone yield (as a function of the relative percentage of the total essential oil yield). The present disclosure provides a catnip plant with elevated levels of E, Z-nepetalactone relative to a wild type plant. For example, a disclosed catnip plant has elevated levels of E, Z-nepetalactone, such as about 45% to 70% as a relative % of the total essential oil, for example about 45% to 60% or 58% to 61% of total essential oils in its chemical profile. In one example, the new catnip variety can exhibit a total E, Z-nepetalactone yield of at least 0.7 g per plant on a dry plant weight basis (e.g., actual absolute quantitative yield per plant on a weight basis adjusted for the specific gravity of the oil which is close to 1). For example, catnip plants provided by the present disclosure can have at least 0.8 g, 0.9 g, 0.95 g, 0.98 g, or 1 g of total E, Z-nepetalactone yield on a dry plant weight basis, or an at least 14%, at least 19%, at least 68%, or at least 92% improvement in total E, Z-nepetalactone yield over a wild type plant or another catnip variety in a growing season. Methods of measuring nepetalactone content of a plant or oil, including E, Z-nepetalactone, are known, and the disclosure is not limited to particular methods. In one example, gas chromatography (GC) and/or mass spectroscopy (MS) is used.

'CR3' also produces significantly more of the minor nepetalactone, E, Z-nepetalactone, when compared to lines that also produce E, Z-nepetalactone. Essential oil from currently cultivated varieties contains many aromatic volatile compounds, including nepetalactone. Catnip cultivar 'CR3' was developed and is distinct from all other commercially available sources because it produces a uniform seeded offspring with the desired characteristics and with a novel chemistry relative to the concentration of E, Z-nepetalactone. The selfed progeny of 'CR3' produce higher essential oil yields and the essential oil is richer in the bioactive isomer E, Z-nepetalactone in these populations and amounts are significantly higher than anything previously reported. 'CR3' provides a superior catnip plant for commercial field production, for dried catnip, or for the distilled aromatic essential oils that have multiple applications, including the pet toy and insect repellent industries.

Thus, provided herein are seeds of the new catnip variety, wherein representative sample seed of the varieties are deposited under ATCC Accession No. PTA-123728. Also provided are catnip seed mixtures containing such seeds, such as mixtures containing other known catnip seeds. The disclosure provides catnip plants having or consisting of the morphological and physiological characteristics of the new catnip variety provided herein. The disclosure also provides catnip plants having one or more of the morphological and physiological characteristics of the new catnip variety (such as those listed in Tables 2-5, and shown in the FIGS.). In one example, such plants have or include the characteristics noted in Table 2, 3, 4, or 5, for example increased amounts E, Z-nepetalactone relative to other varieties. Also provided are seeds of such plants, progeny of such plants, parts of such plants (such as pollen, ovules and cells), and vegetative sprigs or clones of such plants. In one example, the disclosure provides catnip plants having the genotype of one or more of the new catnip variety provided herein. For example, the disclosure provides plants produced by growing the seed of the new catnip variety provided herein.

The disclosed new catnip variety and seeds can be used to produce other catnip plants and seeds, for example as part of a breeding program. Choice of breeding or selection methods using to generate new catnip plants and seeds can depend on the mode of plant reproduction, the heritability of the trait(s) being improved, and the type of variety used commercially (e.g., $F_1$ hybrid variety, pure line variety, etc.). For highly heritable traits, a choice of superior individual plants evaluated at a single location can be effective, whereas for traits with low heritability, selection can be based on mean values obtained from replicated evaluations of families of related plants. Exemplary selection methods commonly include pedigree selection, modified pedigree selection, mass selection, recurrent selection and backcrossing.

The complexity of inheritance influences choice of the breeding method. Backcross breeding can be used to transfer one or a few favorable genes for a highly heritable trait into a desirable variety. This approach has been used extensively for breeding disease-resistant varieties (e.g., see Bowers et al., 1992. *Crop Sci.* 32(1):67-72; Nickell and Bernard, 1992. *Crop Sci.* 32(3):835). Various recurrent selection techniques can be used to improve quantitatively inherited traits controlled by numerous genes.

Promising advanced breeding lines can be thoroughly tested and compared to appropriate standards in environments representative of the commercial target area(s) for generally three or more years. The best or most preferred lines are candidates for new commercial varieties. Those still deficient in a few traits may be used as parents to produce new populations for further selection.

One method of identifying a superior plant is to observe its performance relative to other experimental plants and to one or more widely grown standard varieties.

Plant breeding can result in new, unique and superior catnip varieties and hybrids from the disclosed new catnip variety. Two or more parental lines can be selected (such as new catnip variety as one of the lines), followed by repeated selfing and selection, producing many new genetic combinations. Each year, the germplasm to advance to the next generation is selected. This germplasm is grown under unique and different geographical, climatic and soil conditions, and further selections are then made, during and at the end of the growing season.

The development of new catnip varieties from new catnip variety involves the development, identification, and selection of promising/interesting catnip varieties with desirable traits/characteristics, the continued growing out of those selections and elimination of those not meeting criteria of the plant developer and/or as needed the crossing of these varieties and selection of progeny from the superior hybrid crosses. A hybrid seed is produced by manual crosses between selected male-fertile parents or by using male sterility systems. Hybrids can be identified by using certain single locus traits such as flower color, pubescence color or herbicide resistance which indicate that the seed is truly a hybrid. Additional data on parental lines as well as the phenotype of the hybrid can influence a decision whether to continue with the specific hybrid cross.

Pedigree breeding and recurrent selection breeding methods can be used to develop varieties from breeding populations. Breeding programs combine desirable traits from two or more varieties or various broad-based sources into breeding pools from which varieties are developed by selfing and selection of desired phenotypes. Pedigree breeding is commonly used for the improvement of self-pollinating crops. Two parents (e.g., wherein one of the parents is one of the new varieties provided herein) which possess favorable, complementary traits are crossed to produce an $F_1$. An F2 population is produced by selfing one or several $F_1$'s. Selection of the best or most preferred individuals can begin in the $F_2$ population (or later depending upon the breeding objectives); then, beginning in the $F_3$, the best or most preferred individuals in the best families can be selected. Replicated testing of families can begin in the $F_3$ or $F_4$ generation to improve the effectiveness of selection for traits with low heritability. At an advanced stage of inbreeding (e.g., $F_6$ and $F_7$), the best lines or mixtures of phenotypically similar lines can be tested for potential commercial release as new varieties.

Mass and recurrent selections can be used to improve populations of either self- or cross-pollinating crops. A genetically variable population of heterozygous individuals is either identified or created by intercrossing several different parents. The best or most preferred plants are selected based on individual superiority, outstanding progeny, or excellent combining ability. The selected plants are intercrossed to produce a new population in which further cycles of selection are continued.

Backcross breeding has been used to transfer genetic loci for simply inherited, highly heritable traits into a desirable homozygous variety which is the recurrent parent (e.g., the new variety disclosed herein). The source of the trait to be transferred is called the donor or nonrecurrent parent. The resulting plant is typically expected to have the attributes of the recurrent parent (e.g., variety) and the desirable trait transferred from the donor parent. After the initial cross, individuals possessing the phenotype of the donor parent are selected and repeatedly crossed (backcrossed) to the recurrent parent. The resulting plant is typically expected to have the attributes of the recurrent parent (e.g., variety) and the desirable trait transferred from the donor parent.

The single-seed descent procedure can refer to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population are represented by a progeny when generation advance is completed.

In a multiple-seed procedure, one or more seeds from each plant in a population are commonly harvested and threshed together to form a bulk. Part of the bulk is used to plant the next generation and part is put in reserve. The multiple-seed procedure makes it possible to plant the same number of seeds of a population each generation of inbreeding. Sufficient numbers of seeds are harvested to make up for those plants that did not germinate or produce seed.

Descriptions of other breeding methods that are commonly used for different traits and crops can be found in one of several reference books (e.g., Allard. 1960. Principles of plant breeding. Davis, Calif.: John Wiley & Sons, NY, University of California, pp. 50-98; Simmonds. 1979. Principles of crop improvement. New York: Longman, Inc., pp. 369-399; Sneep and Hendriksen. 1979. "Plant breeding perspectives." Wageningen (ed.), Center for Agricultural Publishing and Documentation; Fehr. 1987).

Breeding New Catnip Varieties with Increased E, Z-nepetalactone

Methods for crossing the new 'CR3' variety provided herein with itself or a second plant are provided, as are the seeds and plants produced by such methods. Such methods can be used for propagation of the new 'CR3' variety provided herein, or can be used to produce hybrid catnip seeds and the plants grown therefrom. Hybrid catnip plants can be used, for example, in the commercial production of catnip products (including biomass and extracts) or in breeding programs for the production of novel catnip varieties. A hybrid plant can also be used as a recurrent parent at any given stage in a backcrossing protocol during the production of a single locus conversion (for example introduction of one or more desirable traits) of the new catnip variety provided herein.

Methods of producing catnip plants and/or seed are provided. Such methods can include crossing the new 'CR3' variety provided herein with itself or a second catnip plant and harvesting a resulting catnip seed, such as an $F_1$ hybrid seed. The resulting plant can be grown, resulting in a catnip plant or part thereof.

In one example methods of producing an inbred catnip plant derived from a new catnip variety provided herein are provided. In one example such methods include (a) generating a progeny plant derived from a new catnip variety provided herein by crossing a plant of the new variety with a catnip plant of a second variety; (b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional at least 2 generations (such as at least 3, at least 4, at least 5, at least 6, at least 7, at least 8 at least 9, at least 10, at least 15 or at least 20, such as 2 to 10, 3 to 10, or 3 to 15 generations) with sufficient inbreeding to produce an inbred catnip plant derived from a new catnip variety provided herein.

The second plant crossed with a new catnip variety provided herein for the purpose of developing novel catnip varieties, is typically a plant which either themselves exhibit one or more desirable characteristics or which exhibit one or more desired characteristic(s) when in hybrid combination. In one example, the second catnip plant is transgenic. Exemplary desired characteristics include, but are not limited to: increased seed yield, increased seedling vigor, modified maturity date, desired plant height, high anthocyanin content, high phenolic content, herbicide tolerance or resistance, drought tolerance or resistance, heat tolerance or resistance, low or high soil pH level tolerance, salt tolerance or resistance, resistance to an insect, resistance to a bacterial disease, resistance to a viral disease, resistance to a fungal disease, resistance to a nematode, resistance to a pest, male sterility, site-specific recombination, abiotic stress tolerance, and increased E, Z-nepetalactone.

When a new catnip variety provided herein is crossed with another different variety, first generation ($F_1$) catnip progeny are produced. The hybrid progeny are produced regardless of characteristics of the two varieties produced. As such, an $F_1$ hybrid catnip plant can be produced by crossing a new catnip variety provided herein with any second catnip plant. The second catnip plant can be genetically homogeneous (e.g., inbred) or can itself be a hybrid. Therefore the disclosure provides any $F_1$ hybrid catnip plant produced by crossing a new catnip variety provided herein with a second catnip plant (such as a transgenic plant having one or more genes that confer to the plant one or more desired characteristics).

Catnip plants can be crossed by either natural or mechanical techniques. Natural pollination occurs in catnip either by self-pollination or natural cross pollination, which typically is aided by pollinating organisms. In either natural or artificial crosses, flowering and flowering time can be a consideration.

Sensitivity to day length can be a consideration when genotypes are grown outside of their area of adaptation. When genotypes adapted to tropical latitudes are grown in the field at higher latitudes, they may not mature before frost occurs. Plants can be induced to flower and mature earlier by creating artificially short days or by grafting. Catnip plants can be grown in winter nurseries located at sea level in tropical latitudes where day lengths are shorter than their critical photoperiod. The short day lengths and warm temperatures encourage early flowering and seed maturation. Early flowering can be useful for generation advance when only a few self-pollinated seeds per plant are desired, but usually not for artificial hybridization because the flowers self-pollinate before they are large enough to manipulate for hybridization. Artificial lighting can be used to extend the natural day length to about 14.5 hours to obtain flowers suitable for hybridization and to increase yields of self-pollinated seed. The effect of a short photoperiod on flowering and seed yield can be partly offset by altitude. At tropical latitudes, varieties adapted to the northern U.S. perform more like those adapted to the southern U.S. at high altitudes than they do at sea level. The light level for delay of flowering can be dependent on the quality of light emitted from the source and the genotype being grown. For example, blue light with a wavelength of about 480 nm typically needs more than about 30 times the energy to inhibit flowering as red light with a wavelength of about 640 nm (Parker et al. 1946. *Bot. Gaz.* 108:1-26).

Temperature can also affect the flowering and development of plants. It can influence the time of flowering and suitability of flowers for hybridization. Artificial hybridization is typically successful between about 26° C. and about 32° C.

Self-pollination can occur naturally in catnip with no manipulation of the flowers. In some examples, the crossing of two catnip plants is accomplished using artificial hybridization. In artificial hybridization, the flower used as a female in a cross is manually cross pollinated prior to maturation of pollen from the flower, thereby preventing self-fertilization, or alternatively, the male parts of the flower are emasculated using known methods. Exemplary methods for emasculating the male parts of a catnip flower include physical removal of the male parts, use of a cytoplasmic or genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed, for example with forceps. Immature buds, such as those hidden under the stipules at the leaf axil, are removed. The calyx is removed, for example by grasping a sepal with the forceps, pulling it down and around the flower, and repeating the procedure until the five sepals are removed. The exposed corolla is removed, for example by grasping it just above the calyx scar, then lifting and wiggling the forceps simultaneously. The ring of anthers is visible after the corolla is removed, unless the anthers were removed with the petals. Cross-pollination can then be performed using, for example, petri dishes or envelopes in which male flowers have been collected. Desiccators containing calcium chloride crystals are used in some environments to dry male flowers to obtain adequate pollen shed.

Emasculation is not necessary to prevent self-pollination (Walker et al. 1979. *Crop Sci.* 19:285-286). When emasculation is not used, the anthers near the stigma can be removed to make the stigma visible for pollination. The female flower is usually hand-pollinated immediately after it is prepared; although a delay of several hours does not reduce seed set. Pollen shed typically begins in the morning and can end when temperatures are above about 30° C. Pollen shed can also begin later and continue throughout much of the day with more moderate temperatures.

Pollen is available from a flower with a recently opened corolla, but the degree of corolla opening associated with pollen shed can vary during the day. In many environments, collection and use of male flowers immediately without storage can be conducted. In the southern U.S. and other humid climates, pollen shed occurs in the morning when female flowers are more immature and difficult to manipulate than in the afternoon, and the flowers can be damp from heavy dew. In those circumstances, male flowers are collected into envelopes or petri dishes in the morning, and the open container is typically placed in a desiccator for about 4 hours at a temperature of about 25° C. The desiccator can be taken to the field in the afternoon and kept in the shade to prevent excessive temperatures from developing within it. Pollen viability can be maintained in flowers for up to about 2 days when stored at about 5° C. In a desiccator at about 3° C., flowers can be stored successfully for several weeks; however, varieties can differ in the percentage of pollen that germinates after long-term storage.

Either with or without emasculation of the female flower, hand pollination can be carried out by removing the stamens and pistil from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and high percentages of successful crosses are typically obtained when pollen is clearly visible on the stigma. Pollen shed can be checked by tapping the anthers before brushing the stigma. Several male flowers can be used to obtain suitable pollen shed when conditions are unfavorable, or the same male can be used to pollinate several flowers with good pollen shed.

When male flowers are not collected and dried in a desiccator, the parents of a cross can be planted adjacent to each other. Plants are typically grown in rows about 65 cm to about 100 cm apart. Yield of self-pollinated seed from an individual plant can range from a few seeds to more than about 1,000 as a function of plant density. A density of about 30 plants/m of row can be used when about 30 or fewer seeds per plant is adequate, about 10 plants/m can be used to obtain about 100 seeds/plant, and about 3 plants/m usually results in a high seed production per plant. Densities of about 12 plants/m or less are commonly used for artificial hybridization.

Multiple planting dates about 7 days to about 14 days apart can typically be used to match parents of different flowering dates. When differences in flowering dates are extreme between parents, flowering of the later parent can be hastened by creating an artificially short day. Alternatively, flowering of the earlier parent can be delayed by use of artificially long days or delayed planting. For example, crosses with genotypes adapted to the southern U.S. are made in northern U.S. locations by covering the late genotype with a box, large can, or similar container to create an artificially short photoperiod of about 12 hours for about 15 days beginning when there are three nodes with trifoliate leaves on the main stem. Plants induced to flower early tend to have flowers that self-pollinate when they are small and can be difficult to prepare for hybridization. Grafting can be used to hasten the flowering of late flowering genotypes.

Catnip Plants Having One or More Desired Heritable Traits

The disclosure provides plants of the new catnip variety 'CR3' modified to include one or more desired heritable traits. In some examples, such plants can be developed using backcrossing or genetic engineering (for example by introducing one or more transgenes into the disclosed new catnip variety 'CR3', wherein the transgenes encode one or more desired traits), wherein essentially all of the desired morphological and physiological characteristics of the new catnip variety are recovered (such as increased E, Z-nepetalactone) in addition to a genetic locus transferred into the plant via the backcrossing technique. Plants developed using such methods can be referred to as a single locus converted plant.

In one example, the method of introducing one or more desired traits into one or more of the disclosed catnip variety 'CR3' includes (a) crossing a first plant of catnip variety 'CR3' with a second catnip plant having one or more desired traits to produce $F_1$ progeny plants; (b) selecting $F_1$ progeny plants that have the one or more desired traits to produce selected $F_1$ progeny plants; (c) crossing the selected progeny plants with at least a first plant of the new variety to produce backcross progeny plants; (d) selecting backcross progeny plants that have the one or more desired traits and physiological and morphological characteristics of the new catnip variety to produce selected backcross progeny plants; and (e) repeating steps (c) and (d) one or more times in succession to produce selected second or higher backcross progeny plants that have the one or more desired traits and the physiological and morphological characteristics of the original new catnip variety 'CR3' when grown in the same environmental conditions.

Backcrossing methods can be used to improve or introduce a characteristic into the new catnip variety 'CR3'. The parental catnip plant which contributes the locus for the desired characteristic is termed the "nonrecurrent" or "donor" parent. This terminology refers to the fact that the nonrecurrent parent is used one time in the backcross protocol and therefore does not recur. The parental catnip plant to which the locus or loci from the nonrecurrent parent are transferred is known as the recurrent parent as it is used for several rounds in the backcrossing protocol (Poehlman and Sleper. 1995. "Breeding Field Crops" Ames, Iowa: Iowa State University Press; Sprague and Dudley, eds. 1988. Corn and Improvement, 3rd edition). In a typical backcross protocol, the original variety of interest (recurrent parent, e.g., the new 'CR3' catnip variety disclosed herein) is crossed to a second variety (nonrecurrent parent) that carries the single locus of interest (such as a desirable trait) to be transferred. The resulting progeny from this cross are then crossed again to the recurrent parent and the process is repeated until a catnip plant is obtained wherein essentially all of the desired morphological and physiological characteristics of the recurrent parent (e.g., the new 'CR3' catnip variety disclosed herein) are recovered (such as increased E, Z-nepetalactone) in the converted plant, in addition to the single transferred locus from the nonrecurrent parent.

The goal of a backcross protocol is to alter or substitute a single trait or characteristic in the original variety, such as the new 'CR3' catnip variety disclosed herein. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent can depend on the purpose of the backcross; for example, a major purpose is to add a commercially desirable, agronomically important trait to the plant. The exact backcrossing protocol can depend on the characteristic or trait being altered to determine an appropriate testing protocol. Although backcrossing methods are simplified when the characteristic being transferred is a dominant allele, a recessive allele can also be transferred. In this instance, it can be useful to introduce a test of the progeny to determine if the desired characteristic has been successfully transferred.

In a backcross where the desired characteristic being transferred to the recurrent parent is controlled by a major gene which can be readily evaluated during the backcrossing, it is common to conduct enough backcrosses to avoid testing individual progeny for specific traits such as yield in extensive replicated tests. In general, four or more backcrosses are used when there is no evaluation of the progeny for specific traits, such as yield. As in this example, lines with the phenotype of the recurrent parent can be composited without the usual replicated tests for traits such as yield, in the individual lines.

Catnip varieties can also be developed from more than two parents, for example using modified backcrossing, which uses different recurrent parents during the backcrossing. Modified backcrossing can be used to replace the original recurrent parent with a variety having certain more desirable characteristics, or multiple parents can be used to obtain different desirable characteristics from each.

Many single locus traits are known that are not regularly selected for in the development of a new inbred but that can be improved by backcrossing techniques. Single locus traits can be, but are not necessarily, transgenic. Examples of these traits include, but are not limited to, male sterility, herbicide resistance, abiotic stress tolerance (such as tolerance or resistance to drought, heat, cold, low or high soil pH level, and/or salt), resistance to bacterial, fungal, or viral disease, insect resistance, restoration of male fertility, enhanced nutritional quality, modified phosphorus characteristics, modified antioxidant characteristics, yield stability, and yield enhancement. These comprise genes generally inherited through the nucleus. Thus plants of the new 'CR3' catnip variety disclosed herein, or progeny thereof, that include a single locus conversion (such as one that confers a desired trait) are provided herein.

Direct selection can be applied where the single locus acts as a dominant trait. An example of a dominant trait is the herbicide resistance trait (such as glyphosate resistance). For the selection process, the progeny of the initial cross are sprayed with a herbicide (such as RoundUp® herbicide) prior to the backcrossing. The spraying eliminates any plants which do not have the desired herbicide resistance characteristic; only those plants which have the herbicide resistance gene are used in the subsequent backcross. This process is then repeated for all additional backcross generations.

Selection of catnip plants for breeding may not be dependent on the phenotype of a plant and instead can be based on genetic investigations. For example, a suitable genetic marker can be used which is closely genetically linked to a desired trait. One of these markers can therefore be used to identify the presence or absence of a trait in the offspring of a particular cross, and hence can be used in selection of progeny for continued breeding. This technique is referred to as marker assisted selection. Any other type of genetic marker or other assay which is able to identify the relative presence or absence of a trait of interest in a plant can also be useful for breeding. Procedures for marker assisted selection applicable to plant breeding are well known in the art. Such methods can be useful in the case of recessive traits and variable phenotypes, or where conventional assays are more expensive, time consuming or otherwise disadvantageous. Types of genetic markers which can be used, but are not limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, which is incorporated herein by reference in its entirety), and Single Nucleotide Polymorphisms (SNPs).

Qualitative characters can be useful as phenotype-based genetic markers in catnip; however, some or many may not differ among varieties commonly used as parents. Exemplary genetic markers include flower color, differences in maturity, height, and pest resistance.

Useful or desirable traits can be introduced by backcrossing, as well as directly into a plant by genetic transformation methods. Genetic transformation can therefore be used to insert a selected transgene into the new 'CR3' catnip variety disclosed herein or progeny thereof, or can, alternatively, be used for the preparation of transgenes which can be introduced by backcrossing. Thus, the disclosure provides methods of producing a plant of the new 'CR3' catnip variety disclosed herein, or progeny thereof, that includes one or more added desired traits, for example that include introducing a transgene(s) conferring the one or more desired traits into the new 'CR3' catnip variety disclosed herein or progeny thereof (for example by transformation with a transgene that confers upon the catnip plant the desired trait), thereby producing a plant of the new 'CR3' catnip variety disclosed herein or progeny thereof that includes the one or more added desired traits.

Methods for the transformation of plants, including catnip, are known. Methods for introducing a desired nucleic acid molecule (e.g., transgene), such as DNA, RNA, or inhibitory RNAs, are well known in the art, and the disclosure is not limited to particular methods. Exemplary techniques which can be employed for the genetic transformation of catnip include, but are not limited to, electroporation, microprojectile bombardment, *Agrobacterium*-mediated transformation and direct DNA uptake by protoplasts.

To effect transformation by electroporation, friable tissues, such as a suspension culture of cells or embryogenic callus, can be used. Alternatively, immature embryos or other organized tissue can be transformed directly. In this technique, the cell walls of target cells can be partially degraded by exposing them to pectin-degrading enzymes (pectolyases) or mechanically wound tissues in a controlled manner. Protoplasts can also be employed for electroporation transformation of plants (Bates. 1994. *Mol. Biotechnol.* 2(2):135-145; Lazzeri. 1995. *Methods Mol. Biol.* 49:95-106).

In microprojectile bombardment, particles (such as those comprised of tungsten, platinum, or gold) are coated with nucleic acids and delivered into cells by a propelling force. For the bombardment, cells in suspension are concentrated on filters or solid culture medium. Alternatively, immature embryos or other target cells can be arranged on solid culture medium. The cells to be bombarded are positioned at an appropriate distance below the macroprojectile stopping plate. An exemplary method for delivering DNA into plant cells by acceleration is the Biolistics Particle Delivery System, which can be used to propel particles coated with DNA or cells through a screen, such as a stainless steel or Nytex screen, onto a surface covered with target catnip cells. The screen disperses the particles so that they are not delivered to the recipient cells in large aggregates. A screen intervening between the projectile apparatus and the cells to be bombarded can reduce the size of projectiles aggregate and contribute to a higher frequency of transformation by reducing the damage inflicted on the recipient cells by projectiles that are too large.

*Agrobacterium*-mediated transfer is a method for introducing gene loci into plant cells. DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations (Klee et al. 1985. *Bio. Tech.* 3(7):637-342). Moreover, vectors for *Agrobacterium*-mediated gene transfer have improved the arrangement of genes and restriction sites in the vectors to facilitate the construction of vectors capable of expressing various polypeptide coding genes. Such vectors have convenient multi-linker regions flanked by a promoter and a polyadenylation site for direct expression of inserted polypeptide coding genes. Additionally, *Agrobacterium* containing both armed and disarmed Ti genes can be used for transformation. The use of *Agrobacterium*-mediated plant integrating vectors to introduce DNA into plant cells is known (e.g., Fraley et al. 1985. *Bio. Tech.* 3(7):629-635; U.S. Pat. No. 5,563,055). Briefly, plant tissue (often leaves) is cut into small pieces, e.g. 10 mm×10 mm, and soaked for 10 minutes in a fluid containing suspended *Agrobacterium*. Some cells along the cut will be transformed by the bacterium, which inserts its DNA into the cell, which is placed on selectable rooting and shooting media, allowing the plants to regrow. Some plants can be transformed just by dipping the flowers into suspension of *Agrobacterium* and then planting the seeds in a selective medium.

Transformation of plant protoplasts can also be achieved using methods based on calcium phosphate precipitation, polyethylene glycol treatment, electroporation, and combinations of these treatments (e.g., Potrykus et al. 1985. *Mol. Gen. Genet.* 199(2):169-177; Omirulleh et al. 1993. *Plant Mol. Biol.* 21(3):415-428; Fromm et al. 1986. *Nature.* 319 (6056):791-739; Uchimiya et al. 1986. *Mol. Gen. Genet.* 204(2):207-207; Marcotte et al. 1988. *Nature* 335(6189): 454-457).

In one example, such methods can also be used to introduce transgenes for the production of proteins in transgenic catnip cells. The resulting produced protein can be harvested from the transgenic catnip. The transgene can be harvested from the transgenic plants that are originated or are descended from the new catnip variety disclosed herein, a seed of such a catnip or a hybrid progeny of such a catnip.

Numerous different genes are known and can be introduced into the new catnip variety 'CR3' disclosed herein, or progeny thereof. Non-limiting examples of particular genes and corresponding phenotypes that can be chosen for introduction into a catnip plant are provided herein.

Herbicide Resistance

Numerous herbicide resistance genes are known and can be used with the methods and plants provided herein. In particular examples, a herbicide resistance gene confers tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, chlorophenoxy acetic acid, or combinations thereof.

In one example the herbicide resistance gene is a gene that confers resistance to a herbicide that inhibits the growing point or meristem, such as an imidazalinone or a sulfonylurea. Exemplary genes in this category code for mutant ALS and AHAS enzyme as described, for example, by Lee et al. (1988. *Embryo J.* 7:1241-8) and Miki et al. (1990. *Theoret. Appl. Genet.* 80:449-458).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricin-acetyl transferase (bar) genes) can be used (e.g., see U.S. Pat. No. 4,940,835). Examples of specific EPSPS transformation events conferring glyphosate resistance are described, for example, in U.S. Pat. No. 6,040,497.

DNA molecules encoding a mutant aroA gene are known (e.g., ATCC accession number 39256 and U.S. Pat. No. 4,769,061), as are sequences for glutamine synthetase genes, which confer resistance to herbicides such as L-phosphinothricin (e.g., U.S. Pat. No. 4,975,374), phosphinothricin-acetyltransferase (e.g., U.S. Pat. No. 5,879,903). DeGreef et al. (1989. *Bio/Technology* 61-64) describe the production of transgenic plants that express chimeric bar genes coding for phosphinothricin acetyl transferase activity. Exemplary genes conferring resistance to phenoxy propionic acids and cyclohexones, such as sethoxydim and haloxyfop are the Acct-S1, Accl-S2 and Acct-S3 genes described by Marshall et al. (1992. *Theor Appl Genet.* 83:435-442).

Genes conferring resistance to a herbicide that inhibits photosynthesis are also known, such as, a triazine (psbA and gs+genes) and a benzonitrile (nitrilase gene) (see Przibilla et al., 1991. *Plant Cell.* 3:169-174). Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes et al. (1992. *Biochem. J.* 285:173).

U.S. Patent Publication No: 20030135879 describes dicamba monooxygenase (DMO) from *Pseuodmonas maltophilia*, which is involved in the conversion of a herbicidal form of the herbicide dicamba to a non-toxic 3,6-dichlorosalicylic acid and thus can be used for producing plants tolerant to this herbicide.

The metabolism of chlorophenoxyacetic acids, such as, for example 2,4-D herbicide, is well known. Genes or plasmids that contribute to the metabolism of such compounds are described, for example, by Muller et al. (2006. *Appl. Environ. Microbiol.* 72(7):4853-4861), Don and Pemberton (1981. *J Bacteriol* 145(2):681-686), Don et al. (1985. *J Bacteriol* 161(1):85-90) and Evans et al. (1971. *Biochem J* 122(4):543-551).

Disease Resistance

Plant defenses are often activated by specific interaction between the product of a disease resistance gene (R) in the plant and the product of a corresponding avirulence (Avr) gene in the pathogen. A plant, such as the 'CR3' variety disclosed herein or progeny thereof, can be transformed with cloned resistance gene to engineer plants that are resistant to specific pathogen strains. See, for example Jones et al. (1994. *Science* 266:789) (tomato Cf-9 gene for resistance to *Cladosporium fulvum*); Martin et al. (1993. *Science* 262 (5138):1432-1436) (tomato Pto gene for resistance to *Pseudomonas syringae* pv.); and Mindrinos et al. (1994. *Cell* 78:1089-1099) (*Arabidopsis* RSP2 gene for resistance to *Pseudomonas syringae*).

A viral-invasive protein or a complex toxin derived therefrom can also be used for viral disease resistance. For example, the accumulation of viral coat proteins in transformed plant cells imparts resistance to viral infection and/or disease development effected by the virus from which the coat protein gene is derived, as well as by related viruses. See Beachy et al. (1990. *Annu Rev Phytopathol* 28:451-474). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody can also be used. See, for example, Tavladoraki et al. (1993. *Nature* 366:469-472), which shows that transgenic plants expressing recombinant antibody genes are protected from virus attack.

Logemann et al. (1992. *Bio/Technology* 10:305-308) disclose transgenic plants expressing a barley ribosome-inactivating gene have an increased resistance to fungal disease.

Insect Resistance

One example of an insect resistance gene includes a *Bacillus thuringiensis* (Bt) protein, a derivative thereof or a synthetic polypeptide modeled thereon (e.g., see Geiser et al., 1986. *Gene* 48:109, discloses a Bt Δendotoxin gene). Moreover, DNA molecules encoding Δ-endotoxin genes can be obtained from the ATCC (Manassas, Va.), for example under ATCC Accession Nos. 40098, 67136, 31995 and 31998. Another example is a lectin. See, for example, Van Damme et al. (1994. *Plant Mol Biol* 24(5):825-830), which discloses several *Clivia miniata* mannose-binding lectin genes. A vitamin-binding protein can also be used, such as avidin. See WIPO Publication No. WO 1994/000992, which teaches the use of avidin and avidin homologues as larvicides against insect pests.

In one example the insect resistance gene is an enzyme inhibitor, for example, a protease, proteinase inhibitor, or an a-amylase inhibitor. See, for example, Abe et al. (1987. *J. Biol. Chem.* 262:16793-7; discloses a rice cysteine proteinase inhibitor), Genbank Accession Nos. Z99173.1 and DQ009797.1 which disclose proteinase inhibitor coding sequences, and Sumitani et al. (1993. *Plant Mol. Biol.* 21:985; discloses *Streptomyces nitrosporeus* α-amylase inhibitor). An insect-specific hormone or pheromone can also be used. See, for example, Hammock et al. (1990. *Nature* 344:458-461; discloses juvenile hormone esterase, an inactivator of juvenile hormone).

Still other examples include an insect-specific antibody or an immunotoxin derived therefrom and a developmental-arrestive protein. See Taylor et al. (1994. Seventh Intl. Symposium on Molecular Plant-Microbe Interactions (Edinburgh Scotland), Abstract #497), who described enzymatic inactivation in transgenic tobacco via production of single-chain antibody fragments.

Male Sterility

Genetic male sterility can increase the efficiency with which hybrids are made, in that it can eliminate the need to physically emasculate the catnip plant used as a female in a given cross (Brim and Stuber. 1973. *Crop Sci.* 13:528-530). Herbicide-inducible male sterility systems are known (e.g., U.S. Pat. No. 6,762,344).

Where use of male-sterility systems is desired, it can be beneficial to also utilize one or more male-fertility restorer genes. For example, where cytoplasmic male sterility (CMS) is used, hybrid seed production involves three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the catnip plant is utilized. However, in many cases, the seeds are considered to be a valuable portion of the crop, thus, it is desirable to restore the fertility of the hybrids in these crops. Therefore, the disclosure provides plants of one of the new catnip varieties disclosed herein comprising a genetic locus capable of restoring male fertility in an otherwise male-sterile plant. Examples of male-sterility genes and corresponding restorers which can be employed are well known (see, e.g., U.S. Pat. Nos. 5,530,191 and 5,684,242).

Tissue Cultures and in Vitro Regeneration of Catnip Plants

Tissue cultures of the new catnip variety are provided. A tissue culture includes isolated cells of the same or a different type or a collection of such cells organized into parts of a plant. Exemplary types of tissue cultures include protoplasts, calli and plant cells that are intact in plants or parts of plants, such as embryos, pollen, flowers, leaves, roots, root tips, anthers, meristematic cells, pistil, seed, petiole, stein, ovule, cotyledon, hypocotyl, shoot or stem, and the like. In a particular example, the tissue culture includes embryos, protoplasts, meristematic cells, pollen, leaves or anthers of one of the new catnip varieties disclosed herein. Also provided are catnip plants regenerated from such tissue cultures, wherein the regenerated catnip plant expresses the physiological and morphological characteristics of new catnip variety disclosed herein.

Methods for preparing tissue cultures of regenerable catnip cells and regenerating catnip plants therefrom, are known, such as those disclosed in U.S. Pat. Nos. 4,992,375; 5,015,580; 5,024,944, and 5,416,011. Tissue culture provides the capability to regenerate fertile plants. This can allow, for example, transformation of the tissue culture cells followed by regeneration of transgenic plants. For transformation to be efficient and successful, DNA can be introduced into cells that give rise to plants or germ-line tissue.

Catnip plants can be regenerated using shoot morphogenesis or somatic embryogenesis. Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in shoot morphogenesis may not generate many somatic embryos, while lines that produce large numbers of embryos during an "induction" step may not give rise to rapidly-growing proliferative cultures. In addition to line-specific responses, proliferative cultures can be observed with both shoot morphogenesis and somatic embryogenesis. Proliferation allows a single, transformed cell to multiply to the point that it can contribute to germ-line tissue.

Shoot morphogenesis is a system whereby shoots are obtained de novo from cotyledonary nodes of catnip seedlings (Wright et al., 1986. *Plant Cell Reports* 5:150-154). The shoot meristems form subepidermally and morphogenic tissue can proliferate on a medium containing benzyl adenine (BA). This system can be used for transformation if the subepidermal, multicellular origin of the shoots is recognized and proliferative cultures are utilized. Tissue that can give rise to new shoots are targeted and proliferated within the meristematic tissue to lessen problems associated with chimerism.

Somatic embryogenesis in catnip is a system in which embryogenic tissue is obtained from the zygotic embryo axis (Christianson et al., 1983. *Science* 222:632-634). The embryogenic cultures are proliferative and the proliferative embryos are of apical or surface origin with a small number of cells contributing to embryo formation. The origin of primary embryos (the first embryos derived from the initial explant) is dependent on the explant tissue and the auxin levels in the induction medium (Hartweck et al., 1988. *In Vitro Cell. Develop. Bio.* 24:821-828). With proliferative embryonic cultures, single cells or small groups of surface cells of the "older" somatic embryos form the "newer" embryos.

Embryogenic cultures can also be used for regeneration, including regeneration of transgenic plants.

Methods of Making Extracts from Catnip

The 'CR3' cultivar disclosed herein can be used to generate E, Z-nepetalactone-containing extracts. Such extracts are also provided by the present disclosure.

In one example, catnip plants or any above-ground part of the plant disclosed herein is harvested, for example, after at least 20 days, at least 30 days, at least 45 days, at least 60 days, at least 70 days, at least 90 days, at least 100 days, or at least 120 days of growth (such as after 45 to 100 days, 60 to 100 days, or 50 to 90 days, such as after 60 days or 90 days of growth). The plant can be dried, for example by leaving it in the field to partially dry, or brought indoors to be dried, for example at 37° C. (e.g., by air drying, microwaving, lyophilization, or combinations thereof, such as by using a Powell walk-in forced air dryer) until no further moisture loss is noted under the temperature and pressure and relative humidity of the drying system; or dried to lower moisture levels with increased temperature and/or pressure. The leaves and flowers of the plant can be separated from the stems, for example manually or by machine. Essential oils can be extracted or distilled from the fresh, partially dried or dried leaves and flowers using steam or hydro-distillation. In some examples, solvent extraction and super critical fluids are not used.

The catnip from which an extract is generated can be field-grown, greenhouse grown and cut at any height above the soil, and the plant distilled fresh, partially dried, or more fully dried to obtain the aromatic essential oil. Catnip plants are typically cut once per growing season, but it has been shown that 'CR3' can be harvested (or cut) once or twice per growing season, provided it is grown with ample water, nutrients and under environmental conditions that result in continued plant growth and development following the initial harvest. Once harvested, the plant can be distilled immediately, allowed to be partially dried in full sun, partial sun in the field and then placed into a container for steam or hydro-distillation. Other processes can also be used, including but not limited to, solvent extraction and other methods of drying and extraction. For an extract or dry product, the catnip may be sun dried, dried in shade, with or without artificial heat introduced by different sources, and then allowed to dry before extraction and/or distillation.

Thus, provided herein are 'CR3' essential oil extracts, which can be used alone or in combination with other ingredients (e.g., to form a product or composition), for example as an insect repellant or feline euphoric. In some examples, a 'CR3' essential oil extract includes by percent total essential oils (such as w/w or w/v), at least about 45% E, Z-nepetalactone (such as at least 50%, at least 55%, at least 59%, at least 60%, at least 61%, at least 62%, at least 63%, at least 64%, at least 65%, at least 66%, at least 67%, at least 68%, at least 69%, at least 70%, or at least 75% E, Z-nepetalactone as a percent of the relative total essential oils, such as 45% to 70% E, Z-nepetalactone as a percent of the relative total essential oils, 45% to 65% E, Z-nepetalactone as a percent of the relative total essential oils, or 45% to 60% E, Z-nepetalactone as a percent of the relative total essential oil, in its chemical profile, such as 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74% or 75% E, Z-nepetalactone as a % of the relative total essential oils). In some examples a 'CR3' essential oil extract further includes at least about 0.5% α-pinene as a % of the total essential oil (such as w/w or w/v), such as at least about 1% α-pinene, at least about 2% α-pinene, at least about 2.5% α-pinene, or at least about 3% α-pinene, such as 1% to 5% α-pinene, 2% to 5% α-pinene, or about 3% α-pinene as a % of the total essential oil. In some examples a 'CR3' essential oil extract further includes at least about 20% Z, E-nepetalactone as a % of the total essential oil (such as w/w or w/v), such as at least about 22% Z, E-nepetalactone, at least about 25% Z, E-nepetalactone, at least about 26% Z, E-nepetalactone, at least about 27% Z, E-nepetalactone, at least about 28% Z, E-nepetalactone, or at least about 29% Z, E-nepetalactone, such as 20 to 35% Z, E-nepetalactone, 20 to 30% Z, E-nepetalactone, 25 to 35% Z, E-nepetalactone, 25 to 30% Z, E-nepetalactone, such as 20%, 21%, 22%, 23%, 24%, 25%, 26%, 27%, 28%, 29%, 30%, 31%, 32%, 33%, 34%, or 35% Z, E-nepetalactone as a % of the total essential oil. In some examples a 'C3' essential oil extract further includes at least about 0.5% β-carophyllene as a % of the total essential oil (such as w/w or w/v), such as at least about 1% β-carophyllene, at least about 2% β-carophyllene, at least about 2.5% β-carophyllene, at least about 3% β-carophyllene, or at least 3.5% β-carophyllene, such as 1% to 5% β-carophyllene, 2% to 5% β-carophyllene, or about 3.5% β-carophyllene as a % of the total essential oil.

In some examples, the 'CR3' essential oil extracts include by percent total essential oils (such as w/w or w/v), (1) at least about 45% E, Z-nepetalactone (such as at least 50%, at least 55%, at least 59%, at least 60%, at least 61%, at least 62%, at least 63%, at least 64%, at least 65%, at least 66%, at least 67%, at least 68%, at least 69%, at least 70%, or at least 75% E, Z-nepetalactone as a percent of the relative total essential oils, such as 45% to 70% E, Z-nepetalactone as a percent of the relative total essential oils, 45% to 65% E, Z-nepetalactone as a percent of the relative total essential oils, or 45% to 60% E, Z-nepetalactone as a percent of the relative total essential oil, in its chemical profile, such as 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74% or 75% E, Z-nepetalactone as a % of the relative total essential oils; (2) at least about 0.5% α-pinene as a % of the total essential oil (such as w/w or w/v), such as at least about 1% α-pinene, at least about 2% α-pinene, at least about 2.5% α-pinene, or at least about 3% α-pinene, such as 1% to 5% α-pinene, 2% to 5% α-pinene, or about 3% α-pinene as a % of the total essential oil; (3) at least about 20% Z, E-nepetalactone as a % of the total essential oil (such as w/w or w/v), such as at least about 22% Z, E-nepetalactone, at least about 25% Z, E-nepetalactone, at least about 26% Z, E-nepetalactone, at least about 27% Z, E-nepetalactone, at least about 28% Z, E-nepetalactone, or at least about 29% Z, E-nepetalactone, such as 20 to 35% Z, E-nepetalactone, 20 to 30% Z, E-nepetalactone, 25 to 35% Z, E-nepetalactone, 25 to 30% Z, E-nepetalactone, such as 20%, 21%, 22%, 23%, 24%, 25%, 26%, 27%, 28%, 29%, 30%, 31%, 32%, 33%, 34%, or 35% Z, E-nepetalactone as a % of the total essential oil; and (4) at least about 0.5% β-carophyllene as a % of the total essential oil (such as w/w or w/v), such as at least about 1% β-carophyllene, at least about 2% β-carophyllene, at least about 2.5% β-carophyllene, at least about 3% β-carophyllene, or at least 3.5% β-carophyllene, such as 1% to 5% β-carophyllene, 2% to 5% β-carophyllene, or about 3.5% β-carophyllene as a % of the total essential oil.

Methods of Repelling Insects

The disclosed new catnip 'CR3' and extracts thereof can be used to repel insects, such as those that serve as vectors for harmful pathogens, such as dengue virus, chikungunya virus, Zika virus, Mayaro and yellow fever viruses, West Nile virus, *Borrelia* bacteria, *Plasmodium falciparum, Rickettsia rickettsia* or *Francisella tularensis, Babesia, Anaplasma phagocytophilum*, Powassan virus, and the like. In some examples, at least 60%, at least 65%, at least 70%, at least 75%, at least 80%, at least 85%, at least 90%, at least 95%, at least 98%, at least 99%, or 100% (such as 50 to 99%, 60 to 99% or 75 to 99%) of insects are repelled (for example using the tests provided herein in Examples 4 and 5) by the composition containing the 'CR3' plant or extracts thereof, for example as compared to no treatment.

In one example, use of new catnip 'CR3' and extracts thereof repel insects within at least 1 minute, at least 2 minutes, at least 3 minutes, at least 4 minutes, at least 5 minutes, at least 10 minutes, at least 30 minutes, or at least 1 hour. In one example, use of new catnip 'CR3' and extracts thereof repel insects or at least 30 minutes, at least 1 hour, at least 2 hours, at least 3 hours, at least 4 hours, at least 8 hours, at least 12 hours, at least 18 hours, or at least 24 hours.

Exemplary insects that can be repelled by the new catnip 'CR3' plants and/or extracts thereof include, but are not limited to mosquitoes (such as *Aedes aegypti, Anopheles*

*gambiae, Aedes cretnius, Anopholes stephensi, Anopheles quadrimaculatus, Anopheles albimanus, Culex quinquefasciatus, Culex pipens, Coquillettidia perturbans*); flies (such as *Musca domestica* and *Stomoxys calcitrans*); peach-potato aphid; cockroaches, (such as the American and German cockroach); ticks (such as *Dermacentor variabilis, Rhipicephalus appendiculatus, R. sanguines,* and *Ixodes scapularis*, including those that harbor the bacterium responsible for Lyme disease); subterranean termites (e.g., *Reticulitermes virginica*, such as those that cause damage to homes and other various wood-based structures); house dust mites (such as *Dermatophagoides pteronyssinus* and *Dermatophagoides farinae*); poultry mites; harvester ants; bed bugs and/or fleas (Siphonapetera) or combinations thereof. Thus, in some examples, at least 60%, at least 65%, at least 70%, at least 75%, at least 80%, at least 85%, at least 90%, at least 95%, at least 98%, at least 99%, or 100% (such as 50 to 99%, 60 to 99% or 75 to 99%) of at least one (such as at least 2, at least 3, at least 4 or at least 5, such as 1, 2, 3, 4, 5, 6, 7, 8, 9, or 10) of such insects are repelled (for example using the tests provided herein in Examples 4 and 5) by the composition containing the 'CR3' plant or extracts thereof, for example as compared to no treatment.

Thus, provided are methods of repelling *Aedes aegypti* mosquitoes, such as those carrying dengue virus, chikungunya virus, Zika virus, Mayaro and yellow fever viruses, West Nile virus, using the disclosed 'CR3' plants and/or extracts thereof. Also provided are methods of repelling *Anopholes gambiae*, such as those carrying a vector for malaria (*Plasmodium falciparum*) or dengue fever, using the disclosed 'CR3' plants and/or extracts thereof.

Thus, provided are methods of repelling *Dermacentor variabilis* ticks, such as those carrying *Rickettsia rickettsia* or *Francisella tularensis* bacteria, using the disclosed 'CR3' plants and/or extracts thereof. Also provided are methods of repelling *Ixodes scapularis*, such as those carrying *Borrelia* bacteria, *Babesia, Anaplasma phagocytophilum*, or Powassan virus, using the disclosed 'CR3' plants and/or extracts thereof.

Products Containing Catnip

The disclosure provides products (e.g., insect repellants) that include the 'CR3' cultivar or progeny thereof, such as a biomass or part thereof, such as an oil extract or leaves. In some examples, such products include E, Z-nepetalactone (for example at least 0.01% wt/wt, at least 0.05% wt/wt, at least 0.1% wt/wt, at least 0.5% wt/wt, at least 1% wt/wt, such as 0.01% wt/wt to 1% wt/wt, 0.01% wt/wt to 0.5% wt/wt, 0.1% wt/wt to 1% wt/wt, 0.5% wt/wt to 1% wt/wt, or 0.1 to 0.5% wt/wt E, Z-nepetalactone). In some examples, such products include an essential oil extract from the 'CR3' cultivar, such as compositions or products that include at least 0.01% wt/wt, at least 0.05% wt/wt, at least 0.1% wt/wt, at least 0.5% wt/wt, at least 1% wt/wt, such as 0.01% wt/wt to 1% wt/wt, 0.01% wt/wt to 0.5% wt/wt, 0.1% wt/wt to 1% wt/wt, 0.5% wt/wt to 1% wt/wt, or 0.1 to 0.5% wt/wt 'CR3' essential oil extract. In some examples, the essential oil extract of 'CR3' is part of a spray, lotion, stick, cream, wipe, clip on, or collar, which can be applied to a body (such as a mammal, such as a human, cat or dog) to repel insects. In some examples, the disclosed products include at least one 'CR3' cell and/or 'CR3' nucleic acid molecule (such as genomic DNA or RNA). In some examples, the disclosed products include at least 0.01% wt/wt 'CR3' essential oil extract, such as at least 0.05% wt/wt 'CR3' essential oil extract, at least 0.1% wt/wt 'CR3' essential oil extract, at least 0.5% wt/wt 'CR3' essential oil extract, or at least 1% wt/wt 'CR3' essential oil extract (such as 0.01% wt/wt to 1% wt/wt, 0.01% wt/wt to 0.5% wt/wt, 0.1% wt/wt to 1% wt/wt, 0.5% wt/wt to 1% wt/wt, or 0.1 to 0.5% wt/wt 'CR3' essential oil extract).

In some examples, the 'CR3' essential oil extracts used in the disclosed insect repellants in methods for repelling insects includes by percent total essential oils (such as w/w or w/v), at least about 45% E, Z-nepetalactone (such as at least 50%, at least 55%, at least 59%, at least 60%, at least 61%, at least 62%, at least 63%, at least 64%, at least 65%, at least 66%, at least 67%, at least 68%, at least 69%, at least 70%, or at least 75% E, Z-nepetalactone as a percent of the relative total essential oils, such as 45% to 70% E, Z-nepetalactone as a percent of the relative total essential oils, 45% to 65% E, Z-nepetalactone as a percent of the relative total essential oils, or 45% to 60% E, Z-nepetalactone as a percent of the relative total essential oil, in its chemical profile, such as 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74% or 75% E, Z-nepetalactone as a % of the relative total essential oils). In some examples a 'CR3' essential oil extract further includes at least about 0.5% α-pinene as a % of the total essential oil (such as w/w or w/v), such as at least about 1% α-pinene, at least about 2% α-pinene, at least about 2.5% α-pinene, or at least about 3% α-pinene, such as 1% to 5% α-pinene, 2% to 5% α-pinene, or about 3% α-pinene as a % of the total essential oil. In some examples a 'CR3' essential oil extract further includes at least about 20% Z, E-nepetalactone as a % of the total essential oil (such as w/w or w/v), such as at least about 22% Z, E-nepetalactone, at least about 25% Z, E-nepetalactone, at least about 26% Z, E-nepetalactone, at least about 27% Z, E-nepetalactone, at least about 28% Z, E-nepetalactone, or at least about 29% Z, E-nepetalactone, such as 20 to 35% Z, E-nepetalactone, 20 to 30% Z, E-nepetalactone, 25 to 35% Z, E-nepetalactone, 25 to 30% Z, E-nepetalactone, such as 20%, 21%, 22%, 23%, 24%, 25%, 26%, 27%, 28%, 29%, 30%, 31%, 32%, 33%, 34%, or 35% Z, E-nepetalactone as a % of the total essential oil. In some examples a 'CR3' essential oil extract further includes at least about 0.5% β-carophyllene as a % of the total essential oil (such as w/w or w/v), such as at least about 1% β-carophyllene, at least about 2% β-carophyllene, at least about 2.5% β-carophyllene, at least about 3% β-carophyllene, or at least 3.5% β-carophyllene, such as 1% to 5% β-carophyllene, 2% to 5% β-carophyllene, or about 3.5% β-carophyllene as a % of the total essential oil.

Provided herein is a dried tea, which includes leaves, oil extract, and/or biomass of the 'CR3' cultivar or progeny thereof. Also provided is a liquid tea, produced from leaves, oil extract, and/or biomass of the 'CR3' cultivar or progeny thereof.

Provided herein are pet toys, which include leaves, oil extract, and/or biomass of the 'CR3' cultivar or progeny thereof. For example a dried biomass and/or leaves of the 'CR3' cultivar or progeny thereof can be used as part of a stuffed pet toy, such as one made of fabric and/or plastic. Oil extracts of the 'CR3' cultivar or progeny thereof can also be formulated into a spray, for example to apply to a pet toy. In some examples the leaves, oil extract, and/or biomass of the 'CR3' cultivar or progeny thereof is formulated into a pet collar (e.g., dog or cat collar), for example to use as an insect repellent (e.g., to repel ticks, fleas, and/or mosquitoes).

Provided herein are compositions that include an oil extract from the 'CR3' cultivar or progeny thereof, which includes E, Z-nepetalactone, and in some examples includes DNA and/or protein from the 'CR3' cultivar or progeny thereof. Such a composition can be formulated into a solid, spray or cream, for example to use as an insect repellent or pheromone. Thus, provided herein are insect repellent compositions, such as a candle, spray, gel, wax, or lotion, containing an oil extract from the 'CR3' cultivar or progeny thereof containing E, Z-nepetalactone. Such insect repellent compositions can further include one or more of citronella, geraniol, eucalyptol, PMD, DEET, picaradin, carriers (such as soybean oil and alcohol) and the like. In some examples, the lotion containing the 'CR3' oil extract further includes glycerin, steric acid, and/or other oils. Provided herein are sunscreens containing an oil extract from the 'CR3' cultivar or progeny thereof containing E, Z-nepetalactone. Such sunscreen compositions can further include one or more of PABA, oxybenzone, cinoxate, dioxybenzone, oxybenzone, homosalate, menthyl anthranilate, octocrylene, octyl methooxycinnamate, octyl sailicyate, sulisobenzone, trolamine salicylate, avobenzone, ecamsule, titanium dioxide, and zinc oxide.

In some examples, an insect repellent containing an oil extract from the 'CR3' cultivar or progeny thereof containing E, Z-nepetalactone is more effective as an insect repellent than DEET.

Example 1

Breeding History of 'CR3'

'CR3' was developed after six different randomized complete block growth trials by selecting the best field performing plants that grew the most upright, survived the winters in New Jersey, and produced the highest above-ground biomass and essential oil and E, Z-nepetalactone yields. In 2001, the USDA *N. cataria* germplasm was comparatively grown at the Rutgers Clifford E. & Melda Snyder Research Farm, in Pittstown, N.J. along with a wide range of commercial catnip varieties in a seeded field trial. For two growing seasons, individual plants that were off-types and exhibited poor performance and/or winter injury were removed from the study. In 2002, the remaining plants from the best performing USDA line PI #W6 17691 were allowed to outcross by wind and bees, the seed was collected from the remaining individual plants, and the new advanced breeding line was formed. In 2005, these seeds were sown in a field trial at the Rutgers Fruit and Ornamental Research Extension Center in Cream Ridge N.J., to identify lines with the desired phenotypic characteristics and to evaluate their uniformity. Only the most promising plants were left in the field, all others were removed. In 2006, after the plants were subjected to the winter season and assessed for winter survival, selections were made from this field with respect to biomass and winter survival by taking cuttings of the individual plants and allowing them to self-pollinate in a research greenhouse. In 2007, those selfed seeds were planted in another two-year evaluation at the Rutgers Clifford E. & Melda Snyder Research Farm, in Pittstown, N.J. Selections took place in the second year after the plants were subjected to the winter season. Plant selections were also largely based upon total essential oil production (e.g., yield/plant) and for this variety E, Z-nepetalactone concentration. The most promising selections from 2008 were then clonally evaluated for two additional years in 2010 and 2011 at the same research farm to ensure minimal environmental influence on the variation of essential oil yields and nepetalactone concentration. Those clones were then selfed and the seed was used in the next growth trial in 2013. The genealogy of cultivar 'CR3' is provided in Table 1.

TABLE 1

Genealogy of the new catnip cultivar 'CR3' (*Nepeta cataria*)

| | |
|---|---|
| 2001 | Original seeded field establishment for catnip evaluation of the USDA germplasm and commercial lines including USDA germplasm PI # W6 17691. Evaluation for desired morphological characteristics and the rouging out of poor performing plants was performed. |
| 2002 | Plants remaining in 2002 that successfully overwintered from 2001 and exhibited desired morphological characteristics formed the breeding lines (C244, C245, C246, C47, C248, C249, and G1) and were allowed to outcross. |
| 2005 | The outcrossed seeds from lines (C244, C245, C246, C47, C248, C249, and G1) were sown in a field trial and evaluated for desired phenotypic characteristics as well as the rouging out of poor performing plants. |
| 2006 | Plants remaining from the 2005 field trials and which exhibited desired phenotypic characteristics were selected forming advanced breeding line (CR). CR breeding lines were allowed to self-pollinate in a research greenhouse. |
| 2007 | Specific CR lines were sown in a field growth trial in which individual plants were identified for desired phenotypic characteristics with emphasis on total essential oil yields and chemical profiles of the essential oil. |
| 2008 | Selections of advanced lines including CR3 from the CR breeding lines were made after the 2007 winter with emphasis on essential oil characteristics, winter hardiness, growth habit, and biomass and essential oil yields and chemical profiles. |
| 2010 | Clonal evaluation of CR3 in comparison to other advanced catnip lines for desired morphological characteristics and essential oil analysis was conducted. |
| 2011 | Clonal evaluation of seven advanced breeding lines including CR3 for desired morphological characteristics and essential oil analysis was conducted. Breeding lines were allowed to self-pollinate in a research greenhouse. |
| 2013 | Final seeded evaluation of the selfed, advanced breeding line 'CR3' the five and commercial lines for comparison and to ensure stability of the self-seeded progeny of CR3 and other CR lines. Selection of 'CR3' for the new catnip cultivar *Nepeta cataria* L. 'CR3' |

In 2013, the clones demonstrating uniform production of essential oil yields and nepetalactone concentration had their selfed progeny planted in a final seeded field evaluation that year at the New Jersey Agricultural Experiment Station Clifford E. & Melda Snyder Research Farm, in Pittstown, N.J. The progeny of 'CR3' was field grown and compared to commercial seed companies offering catnip (Johnny's Selected Seeds, Albion, Me.; Ferry Morse, Norton, Mass.; Stokes, Buffalo, N.Y.; Territorial Seed Company, Cottage Grove, Oreg.; Richters Herbs, Goodwood, Ontario, Canada) and other Rutgers CR lines. The land was cultivated by disc plowing and raised beds were then mechanically prepared, followed by the placement of drip irrigation and plastic mulch. The land was fertilized at 900 lbs/acre of 15-15-15 and was irrigated through drip irrigation as needed and as described (Park et al., 2007). The experimental design for 2013 was a randomized complete block design with 10 plants in each of the six lines having their morphological characteristics recorded for each of the three replications. The plants were spaced 61 cm apart within the rows and the rows were spaced 274 cm apart. Once the plants were in full flower, morphological characteristics were recorded, the plants were cut back to the ground level after 10 weeks, and the entire plot was bulk harvested and dried on site at 37° C. using a walk-in forced-air commercial Powell Tobacco dryer converted to the drying of herbs and botanicals. Plant height, plant width, leaf length, leaf width, and dry weights were recorded. Plant height was measured from the soil level to the flowers down the center of the plant. Plant width was determined by measuring the diameter of the plant. Leaf length was the measurement from the tip of the leaf to the beginning of the petiole on the side that connects to the leaf. The width of the leaf was measured at the basal portion of the leaf at the largest diameter. Dry weights were determined by recording the weight after plants had lost all the water at the set unified temperature of 37° C. The plants in the field were allowed to grow again to maturity, at which point they were again bulk harvested as described above and dried on site at 37° C. Essential oil yields were determined by the hydrodistillation of all of the above-ground biomass of the plant using a Clevenger-type distillation unit with 100 g of dry plant matter. The yields were calculated as percent of dry mass (mg essential oil/100 g above-ground biomass). Essential oil analysis was performed by quantitatively comparing the samples using a flame ionization detector and qualitatively by identifying the chemical constituents of the oil with mass spectrometry (Juliani et al., 2008).

Example 2

Physiological and Morphological Characteristics of 'CR3'

The new catnip cultivar has not been observed under all possible environmental conditions to date. Accordingly, it is possible that the phenotype may vary somewhat with variations in the environment, such as temperature, light intensity, and day length, without, however, any variance in genotype.

The color values were determined in July of 2013 under natural light conditions in Pittstown, N.J.

The following descriptions and measurements describe approximately 2-month-old plants produced from seeds. The plants were grown utilizing a soil growth medium, and were then transplanted to a field in Pittstown, N.J. in June of 2014. Measurements and numerical values represent averages of typical plants.

The physiological and morphological characteristics of catnip cultivar 'CR3' are as follows:

Plant Description from Field-Grown Plants

Growth habit and general appearance—Herbaceous perennial, upright mounding with side stems becoming decumbent.

Branching habit—Freely branching. Quantity of branches per plant: Branch—Shape: Square in cross section. Strength: Strong. Texture: Densely pubescent with soft, short hairs.

Root—Fine, freely branching, spreads through rhizomes.

Inflorescence Description

General description—Type: Terminal and lateral cymosely clustered with flowers either sessile or branched in verticillaster arrangement in the upper nodes, florets in clusters. Fragrance: Strong, minty, highly aromatic. Length or height of terminal inflorescences: Peduncle—Shape: Square in cross section. Strength: Strong. Aspect: Erect. Texture: Densely glandular pubescent.

Flower Description

Type—Single, zygomorphic.

Bud—Rate of opening: Generally takes 2 to 3 days for bud to progress from first color to fully open flower.

Bud just before opening—Shape: Obovoid. Corolla—Shape: Bilabiate, upper lip two lobes and lower lip having three lobes, base fused.

Upper lip—Shape: Obovate, highly reflexed. Margin: Entire. Apex: Rounded. Texture of inner surface: Glabrous. Texture of outer surface: Sparsely pubescent.

Lower lip—Shape of lateral lobes: Oblong. Shape of central lobes: Obovate. Margin: Entire. Apex of central lobe: Scalloped. Apex of lateral lobes: Rounded. Texture of upper surface of lateral lobes: Glabrous. Texture of upper surface of central lobe: Densely pubescent at throat opening. Texture of lower surface of lateral and central lobes: Sparsely pubescent Calyx—Shape: Tubular.

Sepals—Shape: Linear. Apex: Acute. Width of lobes: About 1.0 mm. Texture of inner surface: Moderately pubescent. Texture of outer surface: Densely pubescent.

Pedicel—Strength: Strong, flexibleTexture: Densely pubescent.

Reproductive organs—Androecium: Stamen quantity: 4 per flower, adnate to corolla tube. Anther shape: Bi-lobed. Gynoecium: Pistil quantity: 1 per flower, slightly curved. Stigma shape: Cleft, two-parted.

Figure 2:
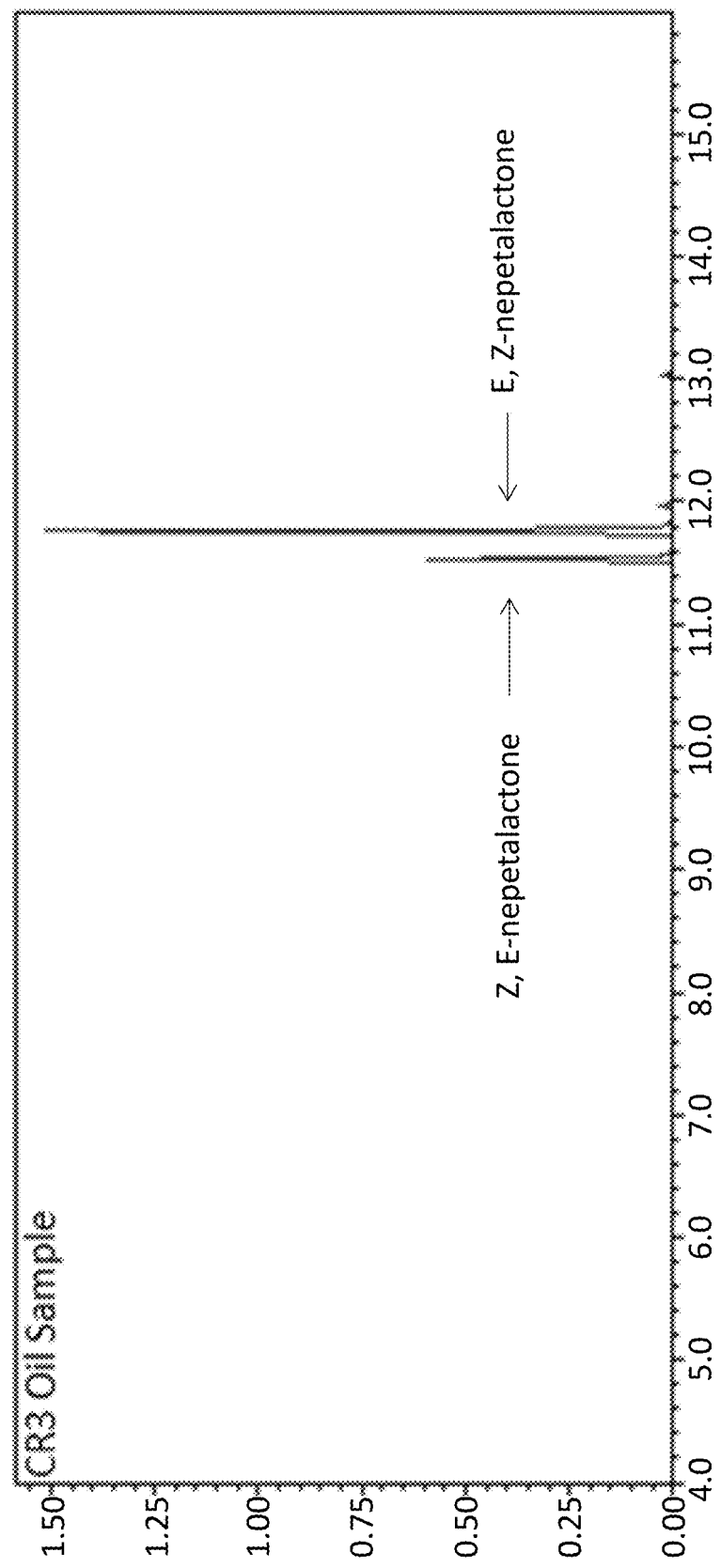
FIG. 2 is the gas chromatogram for results of the essential oil also referred to as the aromatic volatile oil, from catnip cultivar 'CR3' illustrating the peaks of Z, E- and E, Z-nepetalactone.
Figure 3:
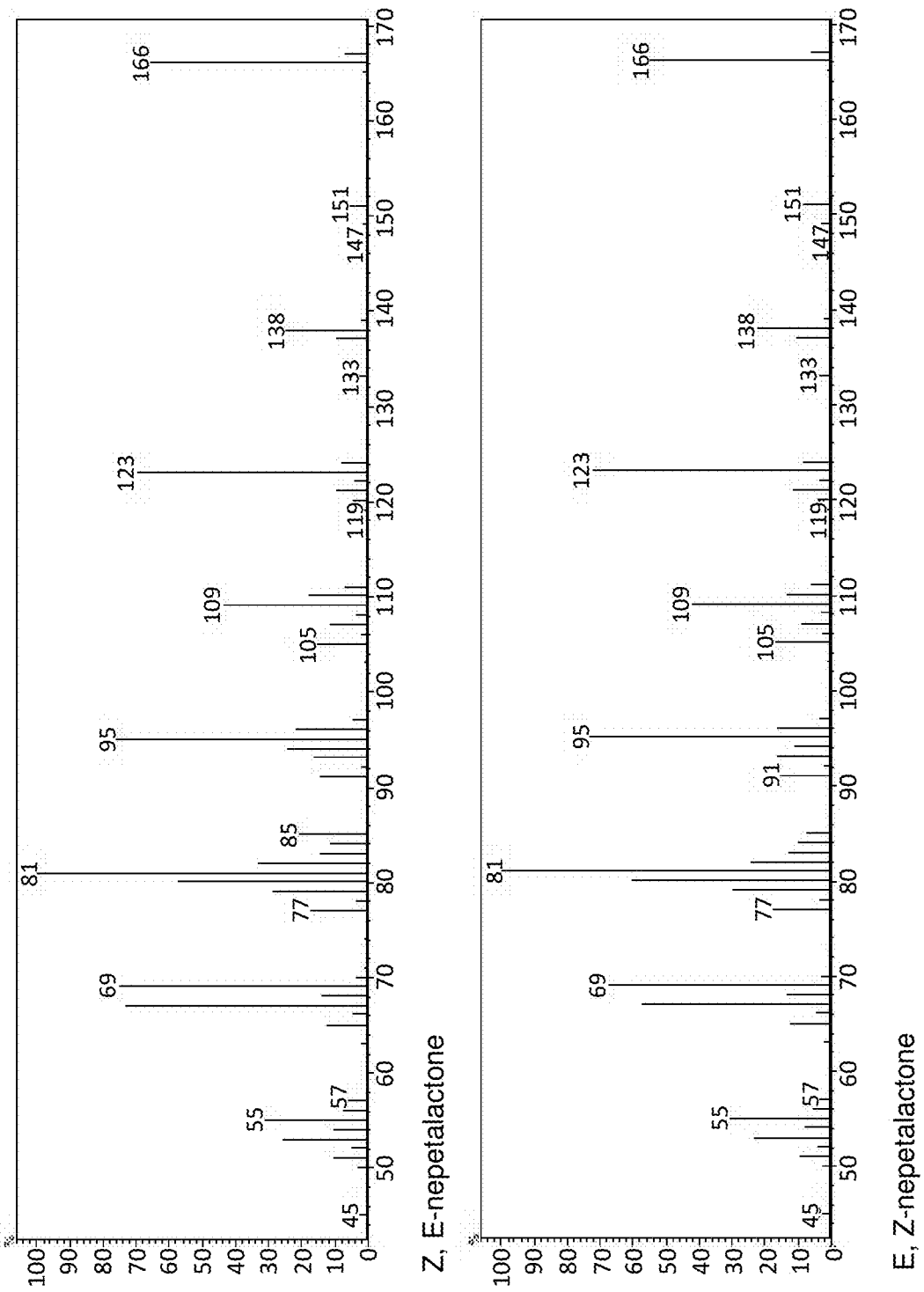
FIG. 3 is the mass spectra data of Z, E- and E, Z-nepetalactone, the major compounds found in the essential oil of catnip 'CR3'.

These plants are bushy and flower within 90 days in the NJ location and environment. Flowering times can vary by location and can be impacted by the seasonal environmental conditions. In central New Jersey's growing zone six (40.559340, −74.961282), this plant can be harvested twice in a growing season for biomass, essential oils, and for E, Z-nepetalactone (Table 2). Catnip cultivar 'CR3' can also be kept from flowering by continual pruning. 'CR3' does not have to be harvested twice in a growing season but the ability for the plant to successfully regrow to the point where a second harvest can take place is economically desirable. Bees, butterflies, and many other insects frequently visited all the catnips, including the progeny of 'CR3' plants during the entire flowering period (FIG. 1). Chemical characterization of the essential oil of these plants using both gas chromatography (GC) and mass spectroscopy (MS) with alkane standards confirmed the presence of Z, E- and E, Z-nepetalactone (FIGS. 2 and 3) (Adams, R. P. (2007). Identification of essential oils by gas chromatography/mass spectrometry. Carol Stream: Allured Publishing Corporation.)

Performance

'CR3' performed far better than selections from each of the commercial seed companies to which it was compared.

'CR3' plants produce about 1.2% essential oil as a percent of dry weight. E Z-nepetalactone yield was 0.98 g per plant on the first harvest and 0.24 g on the second harvest for a total of 1.2 g per year with a 15% improvement over the closest commercial line. 'CR3', unlike most catnips, can be harvested twice each growing season.

As shown in Tables 2 and 3, the concentration of E, Z-nepetalactone was 59% on the first harvest, and 25% on the second harvest, with all catnip lines evaluated exhibiting decreased concentration of E, Z-nepetalactone. The chemical profile of catnip variety 'CR3' is provided in Table 4. 'CR3' survived winter conditions and exhibited the least winter injury and die-back compared to the commercial catnips that were evaluated. As a garden herb, 'CR3' s progeny can live for many additional years on the landscape and could be considered aesthetically attractive with light-green, soft leaves and a highly pleasant spice-like aroma. This new cultivar lends itself more to mechanical harvesting as is required for larger-scale essential oil production and was developed for this purpose. Because of the increased essential oil, commercialization of this catnip cultivar as an essential oil crop is more realistic than prior and currently available catnip lines. 'CR3' could result in significantly increased revenue for those involved in using the essential oil of catnip from the cat and toy industry, to those interested in the use of the oil and/or dry leave as an herbal infusion and tea for health and nutrition purposes and for the insect repellent industry significantly, given that the cultivar was developed as an improved source of essential oil and source of Z, E nepetalactone.

TABLE 2

Morphological and essential oil characteristics of the new catnip cultivar 'CR3' compared to commercial catnip varieties over two harvests, 2013[z].

| 2013 1H w/All Lines | Plant Height (cm) | Plant Spread (cm) | Leaf Length (cm) | Leaf Width (cm) | Dry Weight Per Plant (g) | Oil Yield (g) Per Plant | Z, E Nepetalactone Yield (g) per Plant | E, Z Nepetalactone Yield (g) per Plant |
|---|---|---|---|---|---|---|---|---|
| CR3 | 63.3 A | 95.3 AB | 5.1 A | 4.0 A | 135.7 A | 1.7 A | 0.5 B | 1.0 A |
| JON | 56.5 B | 98.0 AB | 4.7 AB | 3.5 B | 115.0 A | 1.1 B | 0.7 A | 0.3 D |
| RICH | 55.4 B | 100.9 A | 4.8 AB | 3.6 AB | 113.3 AB | 0.9 BC | 0.7 A | 0.1 F |
| STOKES | 53.3 BC | 94.0 AB | 4.9 AB | 3.7 AB | 127.7 A | 1.2 AB | 0.2 C | 0.9 B |
| TERR | 55.9 B | 101.3 A | 4.4 BC | 3.3 B | 112.3 AB | 1.2 AB | 0.2 C | 0.8 C |
| CFM | 50.4 C | 87.5 B | 4.0 C | 3.4 B | 88.0 B | 0.5 C | 0.1 C | 0.3 E |

| 2013 2H w/All Lines | Plant Height (cm) | Plant Spread (cm) | Leaf Length (cm) | Leaf Width (cm) | Dry Weight Per Plant (g) | Oil Yield (g) Per Plant | Z, E Nepetalactone Yield (g) per Plant | E, Z Nepetalactone Yield (g) per Plant |
|---|---|---|---|---|---|---|---|---|
| CR3 | 45.6 A | 82.9 AB | 5.5 A | 3.7 A | 152.0 A | 0.9 A | 0.24 A | 0.59 A |
| CFM | 46.3 A | 89.6 A | 5.7 A | 3.7 A | 136.0 A | 0.8 AB | 0.21 AB | 0.52 AB |
| STOKES | 43.2 AB | 80.6 AB | 5.7 A | 3.6 A | 115.6 A | 0.72 ABC | 0.18 ABC | 0.45 ABC |
| RICH | 43.2 AB | 82.6 AB | 5.4 A | 3.6 A | 157.3 A | 0.62 BCD | 0.16 BCD | 0.39 BCD |
| TERR | 43.2 AB | 77.4 B | 5.9 A | 3.9 A | 101.6 A | 0.50 CD | 0.13 CD | 0.32 CD |
| JON | 39.4 B | 79.7 AB | 5.7 A | 3.8 A | 125.0 A | 0.41 D | 0.10 D | 0.26 D |

[z]CR3 = Rutgers new cultivar release; CFM = Ferry Morse Seeds, Norton, MA; JON = Johnny's Selected Seeds, Albion, ME; RICH = Richters Herbs, Goodwood, Ontario, Canada; STOKES = Stokes Seeds, Buffalo, NY; TERR = Territorial Seed Company, Cottage Grove, OR
[y]Value within columns followed by the different letters are significantly different according to Duncan's test at $P \leq 0.05$.

TABLE 3

Combined Harvest Data for 'CR3' compared to other commercial catnip varieties[z].

| 2013 Second Harvest Lines | Dry Weight Per Plant (g) | Essential Oil Yield (g) Per Plant | E, Z Nepetalactone Yield (g) per Plant | Z, E Nepetalactone Yield (g) per Plant | Total Nep Yield/ Plant |
|---|---|---|---|---|---|
| CR3 | 287 | 2.61 | 1.22 | 1.08 | 2.3 |
| JON | 240 | 1.46 | 0.32 | 1 | 1.32 |
| TERR | 213 | 1.66 | 0.94 | 0.53 | 1.47 |
| RICH | 270 | 1.52 | 0.24 | 1.12 | 1.36 |
| STOKES | 242 | 1.93 | 1.04 | 0.66 | 1.7 |
| CFM | 224 | 1.29 | 0.53 | 0.57 | 1.1 |

[z]CR3 = Rutgers new cultivar release; CFM = Ferry Morse Seeds, Norton, MA; JON = Johnny's Selected Seeds, Albion, ME; RICH = Richters Herbs, Goodwood, Ontario, Canada; STOKES = Stokes Seeds, Buffalo, NY; TERR = Territorial Seed Company, Cottage Grove, Oregon.

TABLE 4

Chemical profile of essential oil from catnip cultivar 'CR3'

| % | Compound Name |
|---|---|
| 3% | α-pinene |
| 29% | Z, E-nepetalactone |
| 59% | E, Z-nepetalactone |
| 3.5% | β-Carophyllene |
| 94.5% | Total |

Example 3

Effect of 'CR3' on Repelling Mosquitoes

This example describes methods used to demonstrate that the disclosed 'CR3' cultivar extracts can be used to repel insects that serve as vectors for pathogens, such as mosquitoes (including *Aedes aegypti* and *Anopholes gambiae*). For example, *Aedes aegypti* is a vector for several diseases, including dengue fever, chikungunya, Zika fever, Mayaro and yellow fever viruses, West Nile virus, and other diseases. *Anopholes gambiae* is a vector for several diseases, including malaria and dengue fever.

Methods

*Nepeta cataria* Cultivation and Essential Oil Preparation

The clonal population serving as source material for the essential oil was the 'CR3' cultivar. The hydro-distilled essential oil from this population was used as the source for the crude essential oil treatment and was partitioned for subsequent fractionation and nepetalactone purification. The clones were transplanted to the field. Immediately before the plants were in full flower, they were harvested and dried at 37° C. with an onsite Powell walk-in forced air heat dryer kept under low heat conditions. Once the plants had lost all moisture, under the temperature and pressure conditions, the leaves and flowers were separated from the stems for hydro-distillation. Essential oils were extracted by hydro-distilling 60 g of dried *N. cataria* leaves and flowers. They were distilled in a 2 L round bottom flask for 3 hours in 1 L of water and the essential oil was collected in a Clevenger-type trap. The essential oils were then prepared and analyzed by GC/MS. The CR3 essential oil contained about 29% Z, E-nepetalactone and about 59% E, Z-nepetalactone (% of the total essential oil).

GC/MS Sample Preparation and Injection Conditions

Essential oil samples were prepared by the extraction 10 µL of crude *N. cataria* essential oil with 1.5 ml of TMBE which was then dried over anhydrous sodium sulfate and centrifuged at 13 Krpm. The supernatant was transferred to a sampling vial for analysis. Essential oil separation was done on a Shimadzu 2010 Plus gas chromatograph equipped with and AOC-6000 auto-sampler and the calculation of the relative abundance of compound fragments was performed on a Shimadzu TQ8040 MS.

The injection volume of 1 µL was separated on a H-Rxi-5Sil MS column heated from 35° C. with a hold of 4 min to 250° C. with a hold of 1.25 min at 20° C./min. The inlet temperature was 250° C. with a split less injection. The ion source temperature was set to 200° C., the interface temperature was set to 250° C., the solvent cut time was 3.5 min, and the detector voltage was set to 0.2 kV with a threshold of 1000. Peak integration percentages were calculated using the GCMS solution v4.3© software from Shimadzu Corporation. Individual compound identities were determined by comparing the mass spectral results to current literature and screening them in the NIST05.LIB, NIST05s.LIB, W10N14.lib and the W10N14R.lib mass spectral libraries.

Mosquito Rearing

Mosquito eggs were reared in water at 27° C. with 80% humidity and the mosquitoes were transferred during the rearing process with an eye dropper. The *Aedes aegypti* eggs were placed in a container holding water and once hatched and formed into larvae, they were separated from the unhatched eggs and placed into fresh water. General fish food tablets were used as the energy source for the maturing mosquitoes. As the mosquitoes began to form into pupae, they were separated from the smaller less developed larvae and placed into fresh water. This container was then placed into a Bug Dorm Cage where the pupae were allowed to mature into adults. Mature females were then separated out of this population of mature adults by aspirating them into a separate container Bug Dorm Cage where they were given a 10% sucrose solution as an energy source. Mature females were kept at these conditions until they were used for experimentation.

Dose Dependent Curve Generation

Repellency was determined by a one-choice landing assay that uses the amount of mosquito landings to calculate the overall effectiveness of the candidate repellent. Twenty, one day starved adult female *Aedes aegypti* mosquitoes were aspirated into a Bug Dorm Cage. Testing was performed between 10:00 am and 4:00 pm PST during *A. aegypti's* host seeking hours. A HotHands® heat pack was used as the heat source to attract the mosquitoes in the upper region of the back panel. Treatments were applied to a Whatman® filter paper and used to wrap the heat source. A control of just acetone was applied to the filter papers before and after each treatment to ensure reproducibility in mosquito behavior. The curve was generated from identifying a concentration of the treatments that exhibited complete repellency and then working in reverse logarithmically. Initial tests showed that few enough landings were observed at 1% generating a greater than 95% reduction in mosquito landings and was defined as complete repellency. Time lapse photography recorded one image every five seconds. A custom was used to count the mosquitoes automatically through the open source image processing software ImageJ.

Results

Figure 4:
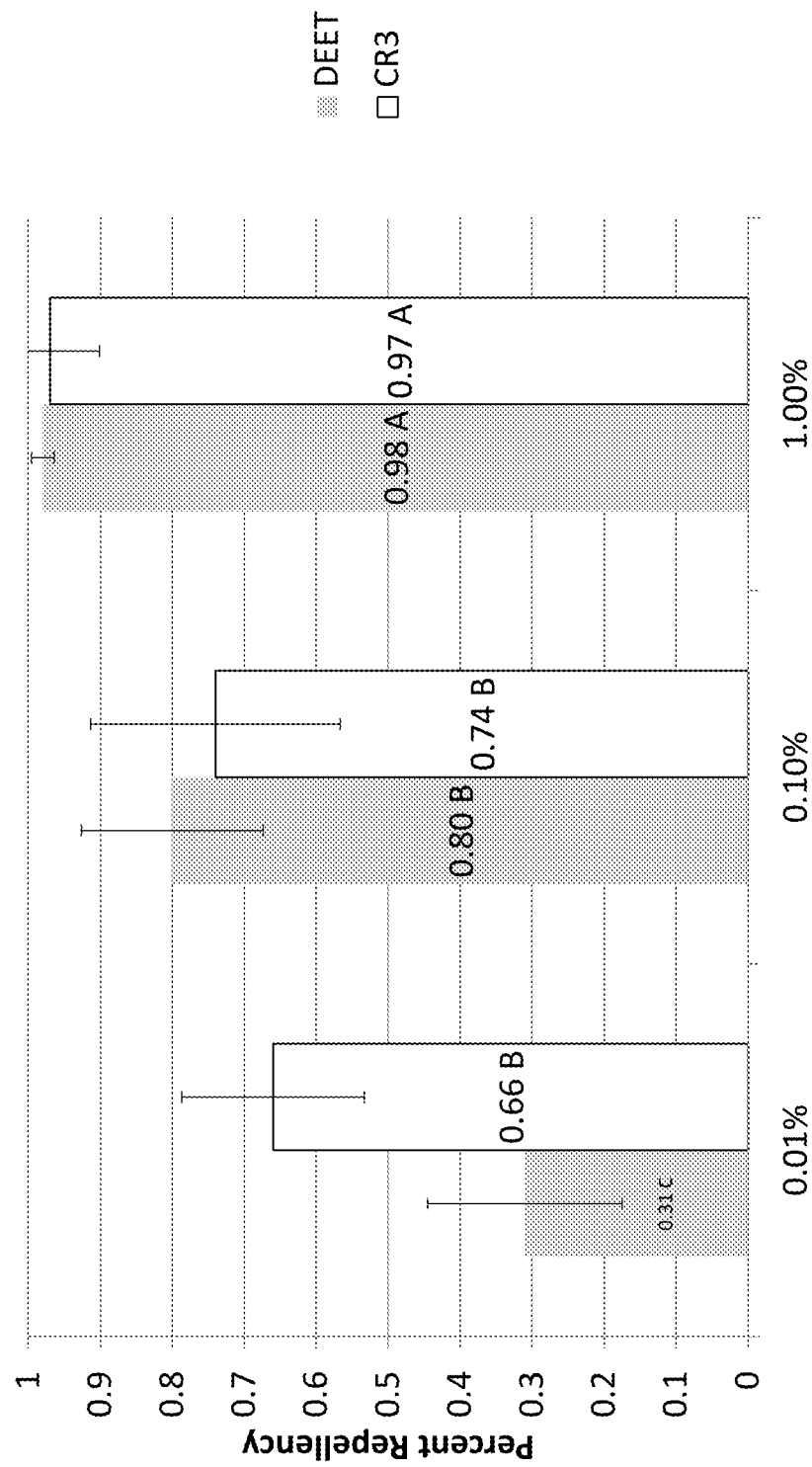
FIG. 4 is a bar graph showing dose response landing inhibition curve for the mosquito species *Aedes aegypti* for the noted repellent treatments at 0.01%, 0.1% and 1%. The treatments included DEET and *N. cataria* 'CR3' crude essential oil. Values within columns followed by the different letters are significantly different according to Duncan's test at $P \leq 0.05$.
Figure 5:
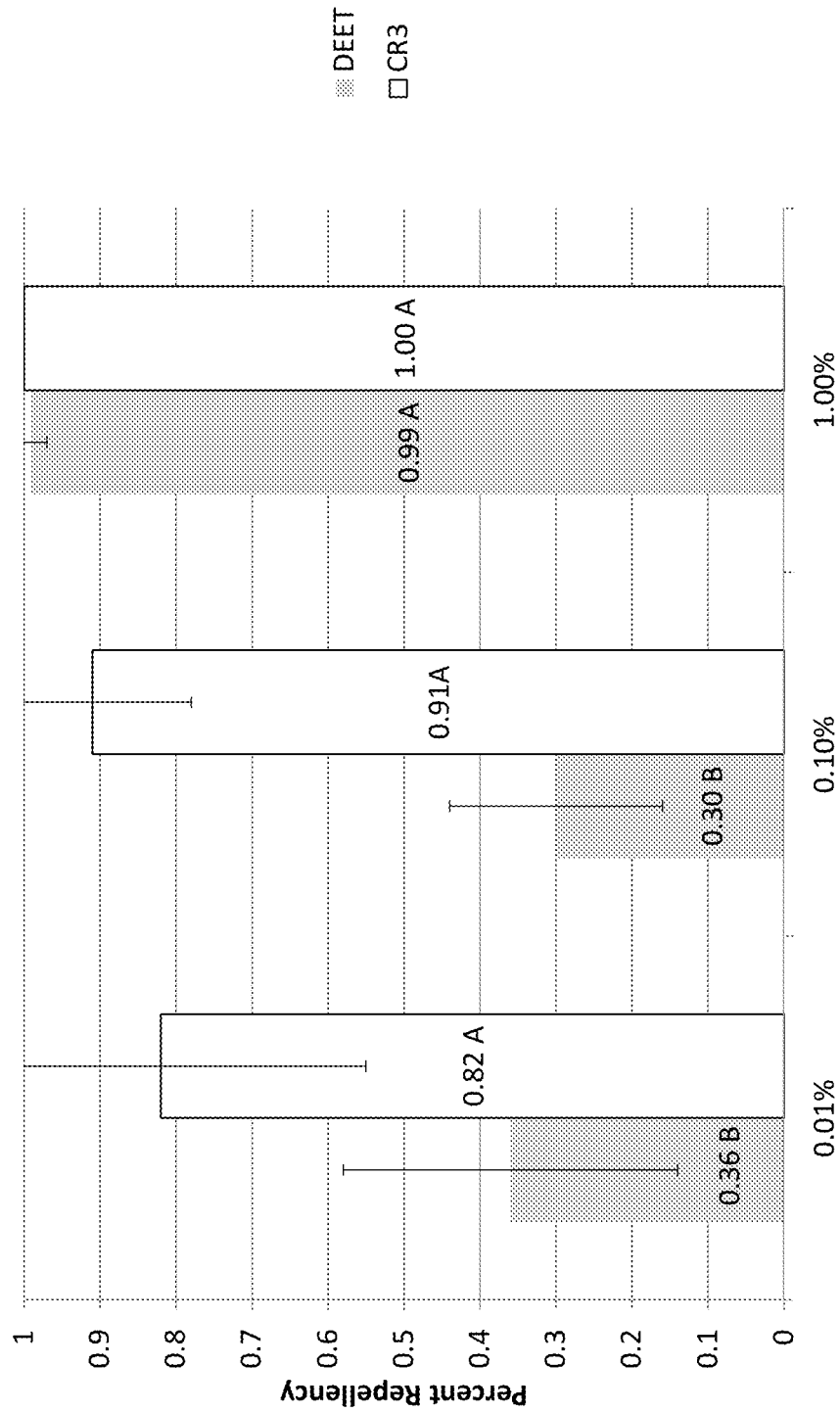
FIG. 5 is a bar graph showing dose response landing inhibition curve for mosquito species *Anopheles A. gambiae* for the various repellent treatments at 0.01%, 0.1% and 1%. The treatments included DEET and *N. cataria* 'CR3' crude essential oil. Values within columns followed by the different letters are significantly different according to Duncan's test at $P \leq 0.05$.

Essential oils prepared from 'CR3' plants exhibited insect repellant properties when tested in a mosquito landing rate inhibition assay against DEET. *Nepeta cataria* plants were evaluated as insect repellents against *Aedes aegypti* and *Anopholes gambiae* mosquitoes in a landing rate inhibition assay against DEET as shown in FIGS. 4 and 5. A dose dependent curve was generated for all treatments. The results indicate that the crude essential oil was able to achieve greater than 95% repellency. At the lowest concentration tested, the crude essential oil sample was more effective than DEET at reducing the number of mosquito landings.

In the dose response curves for both *A. aegypti* and *A. gambiae*, DEET and all of the catnip treatments at 1% decreased the landings of mosquitoes by >95% and all of the 1% treatments grouped together statistically in repellency (FIGS. 4 and 5). At the lowest concentration, all of the catnip extracts were significantly higher than DEET at reducing landings.

As shown in FIG. 4, compositions containing 'CR3' essential oil extracts significantly reduced *A. aegypti* landing by about 65% to nearly 100%, depending on the concentration of the treatment applied to the filter paper. At 0.01% of the treatment applied to the filter paper, 'CR3' essential oil extracts significantly reduced *A. aegypti* landing by about 66%. In contrast, DEET at the same concentration only reduced *A. aegypti* landing by about 32%. In view of this, a composition containing at least 0.01% 'CR3' essential oil, at least 0.1% 'CR3' essential oil, or at least 1% 'CR3' essential oil, can be used as an insect repellent.

As shown in FIG. 5, compositions containing 'CR3' essential oil extracts significantly reduced *Anopholes gambiae* landing by about 80% to nearly 100%, depending on the concentration of the treatment applied to the filter paper. At 0.01%, 'CR3' essential oil extracts significantly reduced *A. gambiae* landing by about 80%. In contrast, DEET at the same concentration only reduced *A. gambiae* landing by about 35%. In view of this, a composition containing at least 0.01% 'CR3' essential oil, at least 0.1% 'CR3' essential oil, or at least 1% 'CR3' essential oil, can be used as an insect repellent.

Based on these results, 'CR3' plants and its essential oils can be used as an effective repellency against a wide range of pests including mosquitoes, vectors of Lyme and other diseases carried by tick species (*Dermacentor variabilis, Rhipicephalus appendiculatus; Ixodes scapularis*; see Example 5 below), and agricultural and household pests.

Example 4

Effect of 'CR3' on Repelling Ticks

This example describes methods used to demonstrate that the disclosed 'CR3' cultivar extracts can be used to repel ticks, such as ticks that serve as vectors for pathogens. *Dermacentor variabilis* is a vector for several diseases including Rocky Mountain spotted fever and tularemia. *Ixodes scapularis* is a vector for several diseases of animals, including humans (e.g., Lyme disease, babesiosis, anaplasmosis, Powassan virus disease, etc.).

Figure 6:
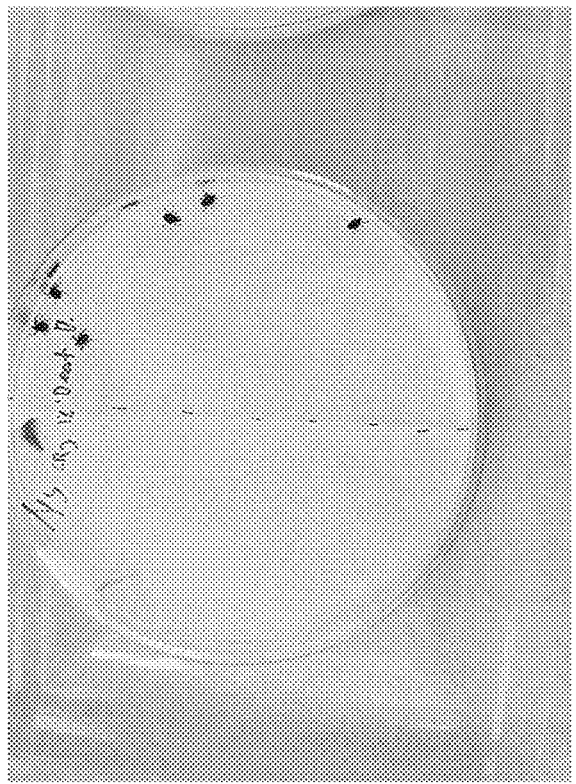
FIG. 6 is a digital image showing how a two choice tick assay was performed. In this example, a 1% acetone extract of 'CR3' essential oil was placed on the left half and an acetone extract of 1% DEET was placed on the right half. Ticks were manually placed on the inside of the petri dish lid on both sides and then the lid placed on bottom part of petri dish.

An arena was constructed out of petri dishes to establish a dose response curve of a repellent ('CR3' essential oil or DEET) filter paper by monitoring the total amount of tick positions over 15 minutes (1 image every 15 sec) and calculating percent repellency. 'CR3' oils were extracted with acetone as described in Example 3. In a one-choice assay, the repellent was applied to half of the filter paper and placed into the petri dish where the ticks are placed, the petri dish cover applied, and the number of ticks counted applied to the repellent zone. In the two-choice repellency test (see FIG. 6), DEET and a repellent ('CR3' essential oil) were applied to different sides of the filter paper and the ticks are counted in reference to the test repellent, not DEET.

Total Tick positions=(# ticks in petri dish)×(60 images)

Percent repellency=[(# of ticks in the repellent zone)/(Total Tick positions)]*100

Three replicates were performed for each treatment. Complete repellency was defined as repelling greater than 95% of the ticks.

Figure 7:
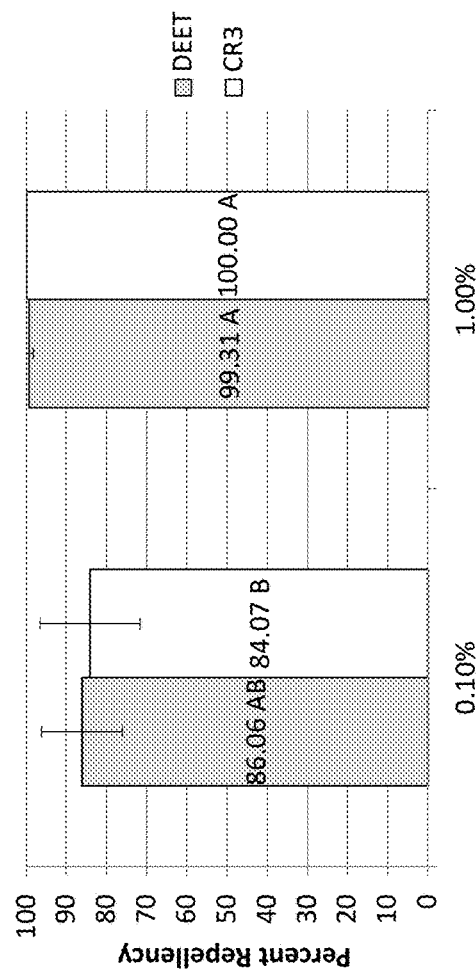
FIG. 7 is a bar graph showing the tick species *Dermacentor variabilis* dose response curve with DEET and 'CR3' essential oil applied at 0.1% and 1%. Values within bars followed by different letters are significantly different according to Duncan's test at $P \leq 0.05$.

As shown in FIG. 7, for the *Dermacentor variabilis* dose response curve, DEET was applied at concentrations 0.1% and 1%, the percent repellency was 86.06±10.2 and 99.31±1.00 respectively. When hydro-distilled 'CR3' essential oil was applied at concentrations 0.1% and 1%, the percent repellency was 84.07±12.47 and 100.00±0.00 respectively. At 1%, DEET and 'CR3' achieved complete repellency and were not significantly different from one another. At 0.1% neither DEET nor 'CR3' achieved complete repellency. At 0.1% DEET was not significantly different from either 1% DEET or 1% 'CR3' essential oil and was not significantly different from 0.1% 'CR3' essential oil. 'CR3' essential oil at 0.1% was significantly different from both 1% DEET and 1% 'CR3' essential oil.

Figure 8:
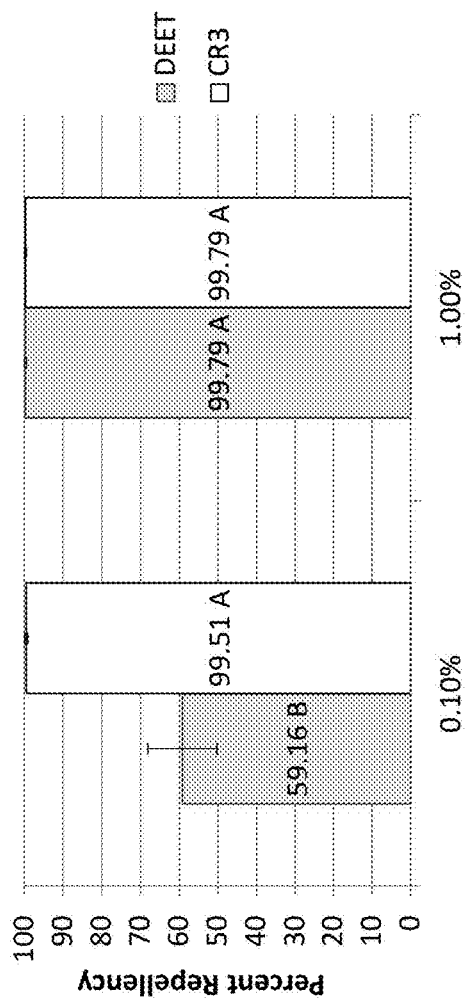
FIG. 8 is a bar graph showing the tick species *Ixodes scapularis* dose response curve with DEET and 'CR3' essential oil applied at 0.1% and 1%. Values within bars followed by different letters are significantly different according to Duncan's test at $P \leq 0.05$.

As shown in FIG. 8, for the *Ixodes scapularis* dose response curve, when DEET was applied at 0.1% and 1%, the percent repellency was 59.16±8.94 and 99.79±0.36 respectively. When hydro-distilled 'CR3' essential oil was applied at 0.1% and 1%, the percent repellency was 99.51±0.43 and 99.79±0.360 respectively. All of the treatments exhibited complete repellency and were not significantly different from one another exhibit when DEET was applied at 0.1%.

Figure 9:
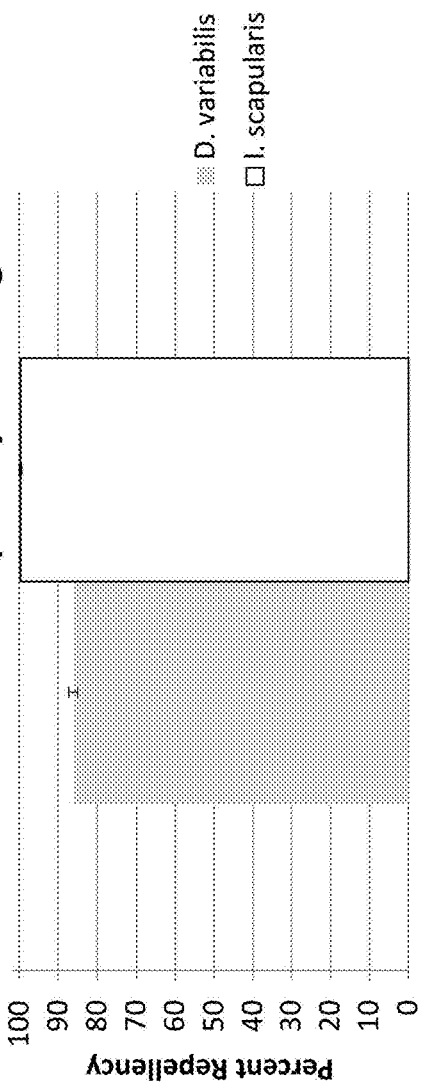
FIG. 9 is a bar graph showing a two choice assay wherein 'CR3' essential oil repelled both tick species, *Dermacentor variabilis* and *Ixodes scapularis* better than DEET.

As shown in FIG. 9, in the two choice assay, 'CR3' essential oil repelled both tick species better than DEET. The 'CR3' essential oil reduced tick counts by 84.86%±1.13 for *D. variabilis* and by 99.72%±0.32 for *I. scapularis*.

In summary, the hydro distilled essential oil of 'CR3' repels *Dermacentor variabilis* and *Ixodes scapularis* with similar efficacy to DEET in a one-choice filter paper assay. In a two-choice assay, both species of ticks were repelled by 'CR3' essential oil to a greater extent than DEET. As a result, the 'CR3' plants and essential oils can be used to *Dermacentor variabilis* is a vector for several diseases including Rocky Mountain spotted fever and tularemia. *Ixodes scapularis* is a vector for several diseases of animals, including humans (e.g., Lyme disease, babesiosis, anaplasmosis, Powassan virus disease, etc.). In view of this, a composition containing at least 0.01% 'CR3' essential oil, at least 0.1% 'CR3' essential oil, or at least 1% 'CR3' essential oil can be used as an insect repellent.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. A method of production, comprising crossing:
   a first parent catnip plant, comprising the variety 'CR3', wherein a representative seed of the variety has been deposited as American Type Culture Collection (ATCC) No. PTA-123728; and
   a second parent catnip plant, comprising a different catnip plant,
   to produce at least one $F_1$ progeny plant.

2. The method of claim 1, wherein the first parent catnip plant further comprises:
   at least 0.85% E, Z-nepetalactone by dry weight;
   at least 45%, at least 50%, or at least 55% E, Z-nepetalactone by percent total essential oils; and/or
   about 1 to 3% α-pinene, about 20 to 35% Z, E-nepetalactone, about 45 to 70% E, Z-nepetalactone and about 1 to 3.5% β-carophyllene, each as a percent of the total essential oils.

3. The method of claim 1, further comprising selecting at least one F1 progeny plant from the crossing that comprises elevated E, Z-nepetalactone content.

4. The method of claim 1, wherein the second parent catnip plant comprises a desired trait, further comprising:
   (a) selecting $F_1$ progeny plants that have the desired trait to produce selected $F_1$ progeny plants;
   (b) crossing the selected $F_1$ progeny plants with plants of the first parent plant variety to produce backcross progeny plants;

(c) selecting backcross progeny plants that have the desired trait and physiological and morphological characteristics of the first parent catnip plant to produce selected backcross progeny plants; and (d) repeating steps (b) and (c) one or more times in succession to produce selected second or higher backcross progeny plants that comprise the desired trait and the physiological and morphological characteristics of the first parent catnip plant when grown in the same environmental conditions.

5. The method of claim 1, wherein the second parent catnip plant is a different variety than the first parent catnip plant, further comprising:
(a) crossing the at least one $F_1$ progeny plant with itself or another plant to produce a seed of a progeny plant of a subsequent generation;
(b) growing a progeny plant of a subsequent generation from the seed, and crossing the progeny plant of a subsequent generation with itself or another plant; and
(c) repeating steps (a) and (b) for an additional 3-10 generations with sufficient inbreeding to produce an inbred catnip plant derived the first parent catnip plant.

6. The method of claim 1, further comprising harvesting the seed from the $F_1$ progeny plant.

7. A composition, comprising a cell from at least one catnip plant, comprising the variety 'CR3', wherein a representative seed of the 'CR3' variety has been deposited as American Type Culture Collection (ATCC) No. PTA-123728.

8. The composition of claim 7, further comprising an essential oil extract from the at least one catnip plant.

9. The composition of claim 8, further comprising one or more of alcohol, water, wax, citronella, geraniol, eucalyptol, PMD, DEET, picaradin, glycerin, steric acid, soybean oil, PABA, oxybenzone, cinoxate, dioxybenzone, oxybenzone, homosalate, menthyl anthranilate, octocrylene, octyl methooxycinnamate, octyl sailicyate, sulisobenzone, trolamine salicylate, avobenzone, ecamsule, titanium dioxide, and zinc oxide.

10. A method of repelling an insect or pest, comprising contacting an insect or applying to a subject the composition of claim 8, thereby repelling insects or pests.

11. The method of claim 10, wherein insects or pests comprise mosquitos, flies, cockroaches, ants, mites, ticks, fleas, other insects or pests, or combinations thereof.

12. A method of making the composition of claim 8, comprising:
(a) hydro-distilling, solvent extracting, super critical fluid extracting, or combinations thereof, biomass, leaves, and/or flowers of the plant of the at least one catnip plant, wherein the biomass, leaves, and/or flowers of the plant are fresh, partially dried, or fully dry; and
(b) collecting essential oils from the dried leaves and flowers, thereby generating the essential oil extract, wherein the essential oil extract comprises at least 45% E, Z-nepetalactone by percent total essential oils.

13. A pet toy comprising the composition of claim 7.

14. A catnip plant comprising a single locus conversion, wherein the single locus conversion is introduced by backcrossing or genetic transformation into catnip plant variety 'CR3', wherein representative seed of the variety 'CR3' has been deposited as American Type Culture Collection (ATCC) No. PTA-123728.

15. A catnip seed comprising a single locus conversion, wherein the single locus conversion is introduced by backcrossing or genetic transformation into catnip plant variety 'CR3', wherein representative seed of the variety 'CR3' has been deposited as American Type Culture Collection (ATCC) No. PTA-123728.

* * * * *